US012186982B2

(12) United States Patent
Beyer et al.

(10) Patent No.: US 12,186,982 B2
(45) Date of Patent: Jan. 7, 2025

(54) SYSTEMS AND METHODS FOR PRINTING A CORE FIBER

(71) Applicant: ASPECT BIOSYSTEMS LTD., Vancouver (CA)

(72) Inventors: Simon Beyer, Richmond (CA); Tamer Mohamed, Richmond (CA); Anas Bsoul, Vancouver (CA); Sheng Pan, Richmond (CA); Sam Wadsworth, Vancouver (CA); Valerio Russo, Vancouver (CA); Suresha Mahadeva, Burnaby (CA); Konrad Walus, Vancouver (CA); Jackson He, Vancouver (CA)

(73) Assignee: ASPECT BIOSYSTEMS LTD.

( * ) Notice: Subject to any disclaimer, the term of this patent is extended or adjusted under 35 U.S.C. 154(b) by 505 days.

(21) Appl. No.: 17/277,992

(22) PCT Filed: Sep. 19, 2019

(86) PCT No.: PCT/CA2019/051338
§ 371 (c)(1),
(2) Date: Mar. 19, 2021

(87) PCT Pub. No.: WO2020/056517
PCT Pub. Date: Mar. 26, 2020

(65) Prior Publication Data
US 2021/0370590 A1    Dec. 2, 2021

Related U.S. Application Data

(60) Provisional application No. 62/733,548, filed on Sep. 19, 2018.

(51) Int. Cl.
*B29C 64/209* (2017.01)
*B29C 64/106* (2017.01)
(Continued)

(52) U.S. Cl.
CPC .......... *B29C 64/209* (2017.08); *B29C 64/106* (2017.08); *B29C 64/35* (2017.08);
(Continued)

(58) Field of Classification Search
CPC ................. B29C 64/106; B29C 64/112; B29C 64/118; B29C 64/124; B29C 64/135; B29C 64/209; B33Y 10/00; B33Y 30/00; B33Y 40/00
See application file for complete search history.

(56) References Cited

U.S. PATENT DOCUMENTS

| 7,033,603 B2 | 4/2006 | Nelson et al. |
| 7,625,198 B2 | 12/2009 | Lipson et al. |

(Continued)

FOREIGN PATENT DOCUMENTS

| CN | 204839829 U | 12/2015 |
| CN | 106671408 A | 5/2017 |

(Continued)

OTHER PUBLICATIONS

Beyer, et al. "3D Alginate Constructs for Tissue Engineering Printed Using a Coaxial Flow Focusing Microfluidic Device," Transducers, Barcelona, Spain, Jun. 16-20, 2013, Downloaded from http://ieeexplore.ieee.org/xpls/icp.jsp? amumber=6626990.
(Continued)

*Primary Examiner* — Jamel M Nelson
(74) *Attorney, Agent, or Firm* — Todd Lorenz

(57) ABSTRACT

A print head, system and method for producing hollow fiber structures, for example three-dimensional biological structures comprising living cells, includes a dispensing channel, a core channel converging with the proximal end of the dispensing channel, a first shell channel converging with the core channel and the dispensing channel at a focusing intersection or chamber, and a sheath flow channel converg-
(Continued)

ing with the dispensing channel at a sheath flow intersection or chamber located between the focusing intersection or chamber and the distal end of the dispensing channel. The diameter of the dispensing channel increases from a first diameter to a second diameter at the sheath flow intersection or chamber, and the core channel has a third diameter less than the first and second diameters. The sheath flow channel includes sheath flow sub-channels and the focusing chamber has a conical frustum shape.

10 Claims, 14 Drawing Sheets

(51) Int. Cl.
 *B29C 64/35* (2017.01)
 *B33Y 10/00* (2015.01)
 *B33Y 30/00* (2015.01)
 *B33Y 40/00* (2020.01)

(52) U.S. Cl.
 CPC .............. *B33Y 10/00* (2014.12); *B33Y 30/00* (2014.12); *B33Y 40/00* (2014.12)

(56) References Cited

U.S. PATENT DOCUMENTS

| | | | |
|---|---|---|---|
| 7,939,003 | B2 | 5/2011 | Bonassar et al. |
| 8,047,235 | B2 | 11/2011 | Lyons et al. |
| 8,636,938 | B2 | 1/2014 | Bonassar et al. |
| 8,785,195 | B2 | 6/2014 | Takeuchi et al. |
| 8,877,112 | B2 | 11/2014 | Bonassar et al. |
| 9,242,031 | B2 | 1/2016 | Bonassar et al. |
| 9,958,088 | B2 | 5/2018 | Lee et al. |
| 2006/0105011 | A1 | 5/2006 | Sun et al. |
| 2008/0070304 | A1 | 3/2008 | Forgacs et al. |
| 2008/0206383 | A1 | 8/2008 | Hull |
| 2010/0060875 | A1 | 3/2010 | Kwon et al. |
| 2011/0006453 | A1 | 1/2011 | Ying et al. |
| 2011/0136162 | A1 | 6/2011 | Sun et al. |
| 2011/0190904 | A1 | 8/2011 | Lechmann |
| 2011/0193259 | A1 | 8/2011 | Howell et al. |
| 2011/0293712 | A1 | 12/2011 | Kurt et al. |
| 2012/0089238 | A1 | 4/2012 | Kang et al. |
| 2012/0322154 | A1 | 12/2012 | Park et al. |
| 2014/0012407 | A1 | 1/2014 | Murphy et al. |
| 2014/0232035 | A1 | 8/2014 | Bheda |
| 2014/0328963 | A1 | 11/2014 | Mark |
| 2015/0174824 | A1 | 6/2015 | Gifford et al. |
| 2016/0136895 | A1* | 5/2016 | Beyer ................ B29C 64/393 425/132 |
| 2016/0288414 | A1* | 10/2016 | Ozbolat ................ C09D 11/30 |
| 2018/0209069 | A1 | 7/2018 | Sun et al. |

FOREIGN PATENT DOCUMENTS

| | | |
|---|---|---|
| CN | 107127971 A | 9/2017 |
| EP | 0605767 A1 | 7/1994 |
| EP | 1790861 A1 | 5/2007 |
| EP | 2489779 A1 | 8/2012 |
| EP | 3398776 A1 | 11/2018 |
| EP | 3670155 A1 | 6/2020 |
| JP | 2008-017798 A | 1/2008 |
| WO | WO 2009/060202 A1 | 5/2009 |
| WO | WO 2011140627 A1 | 11/2011 |
| WO | WO 2012009363 A1 | 1/2012 |
| WO | WO 2012054195 A1 | 4/2012 |
| WO | WO 2012075527 A1 | 6/2012 |
| WO | WO 2013158508 A1 | 10/2013 |
| WO | WO 2014197999 A1 | 12/2014 |
| WO | WO 2015066705 A1 | 5/2015 |
| WO | WO 2015077262 A1 | 5/2015 |
| WO | WO 2016021498 A1 | 2/2016 |
| WO | WO 2017019300 A1 | 2/2017 |
| WO | WO 2018165761 A1 | 9/2018 |
| WO | WO 2019018737 A1 | 1/2019 |
| WO | WO 2020056517 A1 | 3/2020 |

OTHER PUBLICATIONS

Bosnakovski, D., et al., "Chondrogenic Differentiation of Bovine Bone Marrow Mesenchymal Stem Cells (MSCs) in Different Hydrogels: Influence of Collagen Type II Extracellular Matrix on MSC Chondrogensis", Wiley Periodicals Inc. (Feb. 9, 2006).

Choi et al., "Microfluidic fabrication of complex-shaped microfibers by liquid template-aided multiphase microflow," Lab Chip, vol. 11, pp. 1477-1483 (2011).

Ghorbanian, "Microfluidic probe for direct write of soft cell scaffolds," M.Eng. Thesis. McGill University: Canada (2010).

Hong, J.S., "Spherical and cylindrical microencapsulation of living cells using microfluidic devices," Korea-Austria Rheology Journal, vol. 19, No. 3, pp. 157-164 (2007).

Henmi, C., et al., "Development of an Effective Three Dimensional Fabrication Technique Using Inkjet Technology for Tissue Model Samples," Proc. 6th World Congress on Alternatives & Animal Use in the Life Sciences Aug. 21-25, 2007, AATEX 14:689-692 (2008).

Hu et al. "Hydrodynamic spinning of hydrogel fibers," Biomaterials, 31:863-869 (2010).

Hwang et al., "Microfluidic Chip-Based Fabriaction of PLGA Microfiber Scaffolds for Tissue Engineering", Langmuir, vol. 24, pp. 6845-6851 (2008).

Jain, K., et al., "Retrievable, Replaceable, Macroencapsulated Pancreatic Islet Xenografts," Transplantation, vol. 59, No. 3, pp. 319-324 (1995).

Kang et al. "Novel PDMS cylindrical channels that generate coaxial flow, and application to fabrication of nicrofibers and particles", Lab on a Chip, 10:1856-1861 (2010).

Kang et al. "Digitally tunable physicochemical coding of material composition and topography in continuous nicrofibers", Nature Materials, 10:877-883 (2011).

Kang et al., "Microfluidic On the Fly Fabrication of Microstructures for Biomedical Applications", Microfluidic Technolgies fo Human Health, Chapter 12, pp. 293-309 (2012).

Khalil et al., "Bioprinting endothelial cells with alginate for 3D tissue constructs," Journal of Biomechanical Engineering, 131:111002-1-111002-8 (2009).

Kim et al., "Fabrication of cell-encapsulated alginate microfiber scaffold using microfluidic channel", Journal of Manufacturing Science and Engineering, 130:021016-1-021016-6 (2008).

Lee, K.H., et al., "Synthesis of Cell-Laden Hollow Fibers Using Microfluidic Chips and Microvascularized Tissue-Engineering Applications," Wiley InterScience 5(11):1264-68 (2009).

Moon et al., "Tissue Engineering Part C: Methods: Layer by Layer Three-dimensional Tissue Epitaxy by Cell-Laden Hydrogel Droplets," 16(1):157-166 (2010).

Nishiyama et al., "Development of a Three-Dimensional Bioprinter: Construction of Cell Supporting Structures Using Aydrogel and Sate-Of-The-Art Inkjet Technology," Journal of Biomedical Engineering, 131(3):0156-0161 (2009).

Onoe et al., "Core-shell gel wires for the construction of large area heterogeneous structures with biomaterials," EEE MEMS Conference, pp. 248-251 (2010).

Onoe et al., "Metre-long cell-laden microfibres exhibit tissue morphologies and functions," Nature Materials, vol. 12, pp. 584-590 (2013).

Prevost, Ph., et al., "Application of AN69® Hydrogel to Islet Encapsulation: Evaluation in Streptozotocin-induced Diabetic Rat Model," Annals New York Academy of Sciences, vol. 832, Issue 1, pp. 344-349 (Dec. 17, 2006).

Shin et al., "On the flycontinuous generation of alginate fibers using a microfluidic device," Langmuir, 23:9104-9108 (2007).

Takei, T., et al., "Development of mammalian cell-enclosing calcium-alginate hydrogel fibers in a co-flowing stream," Biotechnol. J. vol. 1, pp. 1014-1017 (2006).

(56) References Cited

OTHER PUBLICATIONS

Takei, T., et al., "Novel Technique to Control Inner & Outer Diameter of Calcium Alginate Hydrogel Hollow Microfibers & Immobilization of Mammalian Cells," Biochem. Eng. J. 49:143-147 (2010).

Tanaka, H., et al. "A Novel Immobilization Method for Prevention of Cell Leakage from the Gel Matrix," J. Fermentation & BioEng. vol. 68:216-219 (1989).

Then, K.Y., et al., "A New Technique for Mechanically Characterizing Hydrogels for Tissue Engineering Cornea," Investigative Ophthalmology & Visual Science 46:2185 (2005).

Yamada et al., "Microfluidic synthesis of chemically and physically anisotropic hydrogel microfibers for guided cell growth and networking", Soft Matter, vol. 8, No. 11, pp. 3122-3130 (2012).

Yin, Yu and Ibrahim, Ozbolat, "Cell Viability Characterization of Bioprintable Blood-vessel-like Cellular Channels towards 3D Organ Fabrication", Proceedings of the 2013 Indistrial and Systems Enineering Research Conference, A Krishnamurth and W.K.V. Chan, eds. (2013).

Yu, S.H., et al., "Encapsulation of rat hepatocyte spheroids for the development of artificial liver," Biotech. Tech. vol. 13, pp. 609-614 (1999).

* cited by examiner

| 100 | Core1 inlet |
| 102 | Core2 inlet |
| 104 | Shell1 inlet |
| 106 | Sheath fluid inlet |
| 108 | Fluidic valve |
| 110 | Fluidic focusing intersection 1 |
| 112 | Sheath fluid intersection |
| 114 | Fluid focusing inlet 1 |
| 116 | Third diameter |
| 118 | First diameter |
| 120 | Second diameter |
| 124 | Orifice |

| 100 | Core1 inlet |
| 102 | Core2 inlet |
| 104 | Shell1 inlet |
| 106 | Sheath fluid inlet |
| 108 | Fluidic valve |
| 111 | Fluidic focusing chamber 1 |
| 113 | Sheath fluid chamber |
| 114 | Fluid focusing inlet 1 |
| 116 | Third diameter |
| 118 | First diameter |
| 120 | Second diameter |
| 122 | Dispensing channel |
| 124 | Orifice |

| 100 | Core1 inlet |
| 102 | Core2 inlet |
| 104 | Shell1 inlet |
| 106 | Shell2 inlet |
| 108 | Fluidic valve |
| 110 | Fluidic focusing chamber1 |
| 112 | Sheath Fluid chamber |
| 114 | Fluidic focusing inlet1 |
| 116 | Third diameter |
| 118 | First diameter |
| 120 | Second diameter |
| 122 | Dispensing channel |
| 124 | Orifice |
| 126 | Shell3 inlet |
| 128 | Sheath fluid inlet |
| 130 | Fluidic focusing chamber 2 |
| 132 | Fluidic focusing chamber 3 |

| 100 | Core1 inlet |
| 102 | Core2 inlet |
| 104 | Shell1 inlet |
| 106 | Sheath fluid inlet |
| 108 | Fluidic valves |
| 111 | Fluidic focusing chamber 1 |
| 113 | Sheath fluid chamber |
| 114 | Fluid focusing inlet 1 |
| 116 | Third diameter |
| 118 | First diameter |
| 120 | Second diameter |
| 124 | Orifice |

A

B

SYSTEMS AND METHODS FOR PRINTING A CORE FIBER

CROSS REFERENCE TO RELATED APPLICATIONS

This application claims priority benefit of the filing date of U.S. Provisional Patent Application Ser. No. 62/733,548, filed on Sep. 19, 2018, the disclosure of which application is herein incorporated by reference in its entirety.

FIELD OF THE INVENTION

The present invention relates to systems and methods for producing solid or hollow core fiber structures, and to three-dimensional (3D) printing of such structures from digital files. In some embodiments, the printed fibers comprise living cells.

BACKGROUND OF THE INVENTION

The tissue engineering art has long sought to fabricate viable synthetic structures capable of mimicking and/or replacing living organs and tissues using myriad materials and methods. A lack of pre-patterned vasculature is one of the main factors limiting the success of current tissue engineering strategies, and the current inability to fabricate thick tissue constructs containing endogenous, engineered vasculature or nutrient channels that can integrate with the host tissue is a major technical obstacle preventing the generation and/or implant of larger, viable and/or metabolically active tissues.

3D printing, a form of additive manufacturing, has been applied to create three-dimensional objects directly from digital files, where the object is built up layer-by-layer to achieve the desired three dimensional structure. Initial efforts to adapt these 3D printing techniques to the creation of hollow vessel patterning have focused primarily on the printing and subsequent elimination of sacrificial materials. Bertassoni et al., for example, used a physical method of removing templated agarose from a surrounding cast of a photo-cross-linked acrylated hydrogel such as gelMA. (*Lab Chip* 14:2202 (2014)). The printed agarose fibers showed minimal binding to the GelMA but had to be removed manually, unfortunately, which is time-consuming and difficult and also requires the cast hydrogel to be stronger than the agarose fibers.

An alternative approach involves printing a network of sacrificial fibers from a material that can be subsequently removed via solubilization or liquefaction. Wu et al., for example, printed a 3D perfusable vascular tree by extruding sacrificial Pluronic F127 filaments within a Pluronic F127-diacrylate gel reservoir to provide support during printing (Adv Mater. 2011; 23:H178-183). After photocuring of surrounding acrylate-modified Pluronic F127-diacrylate, the unmodified Pluronic F127 channels could be liquefied by reducing the temperature below its critical micelle temperature, leaving behind perfusable channels. In a similar approach, Lee et al. deposited layers of a collagen supportive matrix around gelatin containing human umbilical vein endothelial cells (HUVECs) (Biomaterials. 2014; 35:8092-8102). Post-printing, the gelatin was melted, which served to "activate" the cell seeding of HUVECs onto the surrounding collagen. Various other sacrificial materials have also been printed, including the "carbohydrate glass" employed by Miller et al. as the sacrificial material, showing subsequent perfusion of the hollow network (Nat Mater. 2012; 11:768-774).

To date, however, the liquifying property of Pluronic 127 at reduced temperatures has made it the most commonly used sacrificial material, and Kolesky and colleagues have successfully employed it with a variety of support materials to create vascularized thick tissue constructs. (Adv Mater. 2014; 26:3124-3130) (co-printing channel structures of Pluronic F127 and cell-loaded gelatin-methacrylate (GelMA); Proc Natl Acad Sci USA. 2016; 113:3179-3184) (Pluronic F127 mixed with thrombin was designated as a "vascular ink" for indirect printing of sacrificial channels within cell-loaded gelatin-fibrinogen bioink). Notably, however, sacrificial materials such as Pluronic F127 are cytotoxic at higher concentrations, and it is unclear what effect the liquified Pluronic will have on surrounding regions of the tissue as it is unlikely that it is removed entirely from the hollow channels.

A more recent alternative to sacrificial hollow-fiber patterning is to use a focused beam of laser light to heat-ablate regions within a pre-cast (or printed) tissue structure. As the laser beam is moved it leaves behind a hollow tunnel, the technique can be relatively fast, can pattern branched hollow tubes in 3D with high resolution, potentially down to the 10-20 um diameter of capillaries. The penetration depth of the beam can be increased by using 2-photon laser light, this also serves to reduce the intensity of out of focus light, so reducing photo-toxicity to areas outside of the ablated channels.

Direct bioprinting of hollow tubes within larger tissues has also been attempted. Gao et al., for example, demonstrated the ability to use coaxial needles to generate and print hollow alginate fibers using calcium chloride cross linking solution in the core of an alginate fiber. The printing nozzle was configured for interior flow of calcium solution with exterior flow of alginate solution (i.e., bioink), creating constructs with endogenous, perfusable microchannels. In this approach, the hollow microchannels were printed onto a stage that progressively lowered into a calcium bath solution for secondary crosslinking. (Biomaterials. 2015; 61:203-215.). An alternative to liquid submersion printing was developed by Hinton et al., employing an extrusion method using a variety of hydrogels for direct structure printing supported in a sacrificial, gelatin-microparticle bath to facilitate crosslinking. (Sci Adv. 2015; 1: e1500758).

Unfortunately, however, the above systems, devices and materials used for conventional 3D bioprinting of hollow fiber networks suffer from a number of shortcomings that prevent their more practical, effective and widespread implementation. As noted above, manual (physical) removal of sacrificial materials is impractical, inconsistent, time-consuming, and probably impossible for smaller vessels. Additionally, patterning vascular channels with sacrificial materials limits the ability to pattern cells and/or biomaterials in an axial manner surrounding the hollow channel. It is difficult to imagine how this technique could be used to fabricate, for example, a patterned network of channels that mimic the structure of real arterioles with smooth muscle cells surrounding the inner layer of endothelial cells.

With laser ablation, the penetration depth is limited to just 1-2 mm and requires optically transparent materials that won't scatter the beam, whereas most cellularised tissues are opaque and light scattering. Finally, with extrusion printing of sacrificial materials, the diameter of the sacrificial fiber (and subsequently the inner diameter of the channels) is dictated by the diameter of the extrusion needle. This diameter is fixed so there is no opportunity to dynamically change the luminal diameter of the channel in different regions of the tissue.

As such, there is a need for systems and devices that can dispense and pattern hollow channels inside 3D tissues, with pro-vasculogenic bioinks and different cell types precisely arranged both axial and parallel to the channel. The technology should be compatible with cell viability, and the inner diameter of the printed channels should be dynamically modifiable ranging from capillaries to larger vessels, within a single tissue construct. For example, it may be desirable to have a larger diameter vessel at the opening of tissue where a perfusion device is attached, then reduce luminal diameter to model smaller vessels inside the tissue. Altering vessel diameter may also be a useful tool to modulate flow changes and limitations in diseases such as atherosclerosis. The current invention addresses these and other unmet needs.

SUMMARY OF INVENTION

Aspects of the invention include systems and methods for producing solid or hollow fiber structures, and for producing three-dimensional (3D) structures from digital files. In some embodiments, the printed fibers comprise living cells. As demonstrated herein for the first time, direct printing of hollow fibers using a core-shell approach can generate hollow fibers with varying diameters as well as multiple shells, and different cell types can be loaded into the different shells in precise axial and parallel arrangements to generate a hollow vessel with multiple cell layers. Additionally, the composition of the vessel wall (cell type and biomaterial composition) can be modified along the length of the channel while continuously printing.

Aspects of the invention include a print head for producing a fiber structure, the print head comprising: a dispensing channel comprising a proximal end having a first diameter and a distal end having a second diameter; a dispensing orifice located at the distal end of the dispensing channel; a core channel having a third diameter converging with the dispensing channel at the proximal end of the dispensing channel, wherein the third diameter of the core channel is less than the first and second diameters of the dispensing channel; a first shell channel converging with the core channel and the dispensing channel at a first fluidic focusing intersection at the proximal end of the dispensing channel; a sheath flow channel converging with the dispensing channel at a sheath fluid intersection located between the first fluidic focusing intersection and the distal end of the dispensing channel, wherein the diameter of the dispensing channel increases from said first diameter to said second diameter at the sheath fluid intersection; wherein the core channel, the first shell channel and the sheath flow channel are in fluid communication with the dispensing channel.

In preferred embodiments, the print head is configured to dispense non-cross-linkable materials through the core channel. In alternative embodiments, the print head is configured to dispense cross-linkable materials through the core channel to create solid fibers.

In some embodiments the first shell channel comprises a plurality (e.g. two, three, four or more) first shell sub-channels that converge toward the dispensing channel via a first fluidic focusing chamber disposed within the print head. In one embodiment the first diameter of the dispensing channel from the first fluidic focusing intersection to the sheath fluid intersection is substantially identical to the diameter of the first fluidic focusing intersection. In a preferred embodiment, the first fluidic focusing chamber comprises a conical frustum shape configured to focus fluid toward the dispensing channel, and the first diameter is substantially identical to the smallest diameter of the frustum at the outlet of the first fluidic focusing chamber.

In some embodiments, the print head further comprises at least a second shell channel converging with the dispensing channel at a second fluidic focusing intersection located between the first fluidic focusing intersection and the sheath fluid intersection. In some embodiments the second shell channel comprises a plurality of second shell sub-channels that converge toward the dispensing channel via a second fluidic focusing chamber. In a preferred embodiment, the second fluidic focusing chamber comprises a conical frustum shape configured to focus fluid toward the dispensing channel, and the first diameter is substantially identical to the smallest diameter of the frustum at the outlet of the second fluidic focusing chamber.

In some embodiments the print head further comprises third, fourth, fifth and/or sixth shell channels converging with the dispensing channel at third, fourth, fifth and/or sixth fluidic focusing intersections located between the second fluidic focusing intersection and the sheath fluid intersection. In some embodiments the third, fourth, fifth and/or sixth shell channel each comprises a plurality of sub-channels that converge toward the dispensing channel via a third, fourth, fifth and/or sixth fluidic focusing chamber. In a preferred embodiment, the third, fourth, fifth, and/or sixth fluidic focusing chamber comprises a conical frustum shape configured to focus fluid toward the dispensing channel, and the first diameter is equal to the smallest diameter of the frustums at the outlet of the chambers.

In some embodiments the sheath flow channel comprises a plurality of sheath flow sub-channels that converge toward the dispensing channel via a sheath fluid chamber. In one embodiment the second diameter of the dispensing channel from the sheath fluid intersection to the dispensing orifice is substantially identical to the diameter of the sheath fluid chamber. In a preferred embodiment, the sheath fluid chamber comprises a conical frustum shape configured to focus fluid toward the dispensing channel, and the second diameter is equal to the smallest diameter of the frustum at the outlet of the chamber.

In one embodiment, the sheath flow channel comprises a sheath fluid input orifice and a control valve; preferably wherein the print head is configured to dispense sheath fluid through the sheath flow channel. In some embodiments, the sheath fluid comprises a chemical cross-linking agent. In some embodiments, the sheath fluid comprises an aqueous solvent.

In one embodiment, the print head comprises at least two core sub-channels, which converge to form a fluid focusing inlet having the third diameter. In an exemplary embodiment, the first core sub-channel comprises a sheath fluid input orifice and a control valve, and the second core sub-channel comprises a buffer solution input orifice and a control valve.

In one embodiment, the first shell channel is concentrically disposed around the core channel. In an exemplary embodiment, the distal end of the core channel comprises a tube (e.g., made of plastic, glass or metal) disposed within the first shell channel in the print head. In some embodiments, the distal end of the core channel comprises a tube having an exterior configured to fit into a portion of the first shell channel and an inner surface (defining a hollow space in the tube) configured to align with the core channel.

In another embodiment, the inventive print head comprises a dispensing channel comprising a proximal end having a first diameter and a distal end having a second diameter; a dispensing orifice located at the distal end of the dispensing channel; a core channel having a third diameter converging with the dispensing channel at the proximal end of the dispensing channel, wherein the third diameter of the core channel is less than the first and second diameters of the dispensing channel; a shell channel concentrically disposed around the distal end of the core channel and converging with the core channel and the dispensing channel at a fluidic focusing chamber at the proximal end of the dispensing channel; a sheath flow channel comprising a plurality of sheath flow sub-channels converging with the dispensing channel at a sheath fluid chamber, wherein the diameter of the dispensing channel increases from said first diameter to said second diameter at the sheath fluid chamber; wherein the core channel, the first shell channel and the sheath flow channel are in fluid communication with the dispensing channel. In an exemplary embodiment, the distal end of the core channel comprises a tube disposed within the shell channel in the print head.

In preferred embodiments, the print head is configured to dispense non-cross-linkable materials through the core channel.

In some embodiments, the print head further comprises an extension tip comprising a tube having an exterior configured to fit into a portion of the dispensing channel and an inner surface (defining a hollow space in the tube) configured to align with the dispensing channel.

In one exemplary embodiment, the third diameter is between about 0.1 and 2 mm, more preferably between about 0.4 and 1.0 mm, most preferably about 0.7 mm. In an exemplary embodiment, the first diameter is between about 0.2 and 3 mm, more preferably between about 1 and 2 mm, most preferably about 1.5 mm. In an exemplary embodiment, the second diameter of the dispensing channel is between about 0.3 and 3.5 mm, more preferably between about 1.5 and 2.5 mm, most preferably about 2 mm. Accordingly, in one exemplary embodiment, the diameter increases incrementally from about 0.7 mm at the fluid focusing inlet, to about 1.5 mm at the proximal end of the dispensing channel, to about 2.0 mm at the distal end of the dispensing channel.

In another exemplary embodiment, the third diameter is between about 0.4 and 1 mm, more preferably between about 0.6 and 0.8 mm, most preferably about 0.7 mm. In an exemplary embodiment, the first diameter is between about 1 and 2 mm, more preferably between about 1.3 and 1.7 mm, most preferably about 1.5 mm. In an exemplary embodiment, the second diameter of the dispensing channel is between about 1.5 and 2.5 mm, more preferably between about 1.8 and 2.2 mm, most preferably about 2 mm. Accordingly, in one exemplary embodiment, the diameter increases incrementally from about 0.7 mm at the fluid focusing inlet, to about 1.5 mm at the proximal end of the dispensing channel, to about 2.0 mm at the distal end of the dispensing channel.

Aspects of the invention include a system for producing a fiber structure, the system comprising: a print head comprising a dispensing channel comprising a proximal end having a first diameter and a distal end having a second diameter; a dispensing orifice located at the distal end of the dispensing channel; a core channel having a third diameter converging with the dispensing channel at the proximal end of the dispensing channel, wherein the third diameter of the core channel is less than the first and second diameters of the dispensing channel; a first shell channel converging with the core channel and the dispensing channel at a first fluidic focusing intersection at the proximal end of the dispensing channel; a sheath flow channel converging with the dispensing channel at a sheath fluid intersection located between the first fluidic focusing intersection and the distal end of the dispensing channel, wherein the diameter of the dispensing channel increases from said first diameter to said second diameter at the sheath fluid intersection; wherein the core channel, the first shell channel and the sheath flow channel are in fluid communication with the dispensing channel.

In some embodiments, the print head is configured to dispense non-cross-linkable materials through the core channel; a receiving surface for receiving a first layer of material dispensed from the print head; and a positioning component for positioning the dispensing orifice of the print head in 3D space, wherein the positioning component is operably coupled to the print head.

In some embodiments, a system further comprises a programmable control processor for controlling the positioning component and for controlling a flow rate of one or more fluids through the print head. In some embodiments, a system further comprises a fluid removal component that is configured to remove an excess fluid that is dispensed from the print head. In some embodiments, the fluid removal component comprises a porous membrane that is configured to allow passage of the excess fluid. In some embodiments, the fluid removal component comprises an absorbent material. In some embodiments, the fluid removal component comprises a vacuum that is configured to aspirate the excess fluid. In some embodiments, the vacuum is applied below the receiving surface. In some embodiments, the vacuum is applied above the receiving surface. In some embodiments, the vacuum is applied through one or more vacuum channels on the print head. In some embodiments, the one or more vacuum channels are positioned near the dispensing orifice on the print head.

In some embodiments, a system further comprises a pressure control component that is configured to regulate the flow rate of the one or more fluids through the print head. In some embodiments, a system further comprises one or more fluid reservoirs that are in fluid communication with the print head. In some embodiments, a fluid reservoir comprises a sheath solution. In some embodiments, the sheath solution comprises a crosslinking solution that is configured to solidify an input material. In some embodiments, the crosslinking solution comprises a divalent cation. In some embodiments, the divalent cation is $Ca^{++}$. In some embodiments, a fluid reservoir comprises a buffer solution. In some embodiments, the buffer solution is miscible with an input material. In some embodiments, a fluid reservoir comprises an input material. In some embodiments, the input material comprises a cross-linkable material, e.g., a hydrogel. In some embodiments, the hydrogel comprises an alginate. In some embodiments, the alginate is a depolymerized alginate. In some embodiments, the input material comprises one or more living cells. In some embodiments, the input material comprises an extra cellular matrix material. In some embodiments, the input material comprises an active agent.

In some embodiments, the print head is configured to produce a constant mass flow rate through the dispensing channel. In some embodiments, a system further comprises a crosslinking component. In some embodiments, the crosslinking component comprises a UV lamp. In some embodiments, the crosslinking component is positioned adjacent to the dispensing orifice.

Aspects of the invention include a method for generating a solidified fiber structure, the method comprising: providing a system for producing a fiber structure, the system comprising: a print head comprising a dispensing channel comprising a proximal end having a first diameter and a distal end having a second diameter; a dispensing orifice located at the distal end of the dispensing channel; a core channel having a third diameter converging with the dispensing channel at the proximal end of the dispensing channel, wherein the third diameter of the core channel is less than the first and second diameters of the dispensing channel; a first shell channel converging with the core channel and the dispensing channel at a first fluidic focusing intersection at the proximal end of the dispensing channel; a sheath flow channel converging with the dispensing channel at a sheath fluid intersection located between the first fluidic focusing intersection and the distal end of the dispensing channel, wherein the diameter of the dispensing channel increases from said first diameter to said second diameter at the sheath fluid intersection; wherein the core channel, the first shell channel and the sheath flow channel are in fluid communication with the dispensing channel.

In some embodiments, the print head is configured to dispense non-cross-linkable materials through the core channel; a receiving surface for a receiving a first layer of material dispensed from the print head; a positioning component for positioning the dispensing orifice of the print head in 3D space, wherein the positioning component is operably coupled to the print head; a programmable control processor for controlling the positioning component and for controlling a flow rate of one or more fluids through the print head; a first fluid reservoir comprising a first input material; a second fluid reservoir comprising a buffer solution; and a third fluid reservoir comprising a sheath solution, wherein the sheath solution comprises a crosslinking solution; wherein the fluid reservoirs are in fluid communication with the print head; passing the first input material through the dispensing channel; crosslinking the first input material with the crosslinking component to generate a solidified fiber structure; and dispensing the solidified fiber structure from the dispensing orifice of the print head.

In preferred embodiments, the methods comprise simultaneously dispensing buffer solution and/or sheath fluid through the core channel, one or more input materials through the one or more shell channels, and sheath fluid through the sheath flow channel so as to form a hollow core in the printed fiber.

In some embodiments, the non-cross-linkable materials in the core channel comprise a buffer solution and the sheath fluid in the sheath flow channel comprises a chemical cross-linking agent, and the contacting occurs at the sheath fluid intersection to solidify an exterior surface of the stream of cross-linkable materials in the dispensing channel.

In some embodiments, the non-cross-linkable materials in the core channel comprise a chemical cross-linking agent and the sheath fluid in the sheath flow channel comprises an aqueous solvent, and the contacting occurs at the first fluidic focusing intersection to solidify an interior surface of the stream of cross-linkable materials in the dispensing channel.

In some embodiments, the non-cross-linkable materials in the core channel comprise a chemical cross-linking agent, and the sheath fluid in the sheath flow channel comprises a chemical cross-linking agent, and the contacting occurs at the first fluidic focusing intersection to solidify an interior surface of the stream of cross-linkable materials and at the sheath fluid intersection to solidify an exterior surface of the stream of cross-linkable materials in the dispensing channel.

In some embodiments, a method further comprises: encoding the programmable control processor with a planar structure to be printed; and depositing a first layer of the solidified fiber structure on the receiving surface to print the planar structure.

In some embodiments, a method further comprises: encoding the programmable control processor with a 3D structure to be printed; and depositing a subsequent layer of the solidified fiber structure on top of the planar structure to print a 3D structure.

In some embodiments, a system further comprises a fourth fluid reservoir comprising a second input material, and a method comprises generating a solidified fiber structure that comprises the second input material. In some embodiments, a method further comprises simultaneously dispensing the first and the second input materials to generate a solidified fiber structure that comprises a mixture of the first and second input materials.

In alternative embodiments, solid core-shell fibers can be made using the same or different cross-linkable materials in the core and in the shell channels, respectively. In the former embodiment, the crosslinker may crosslink the core material by means of diffusion, such as alginate hydrogel being crosslinked by one or more crosslinking agents, or alternatively may be cross-linked in the presence of light. In the latter embodiment, the core channel comprises a cross-linkable material that may be solidified some time after being dispensed from the print head, while the shell channel comprises a different cross-linkable material that is solidified upon printing.

Figure 1:
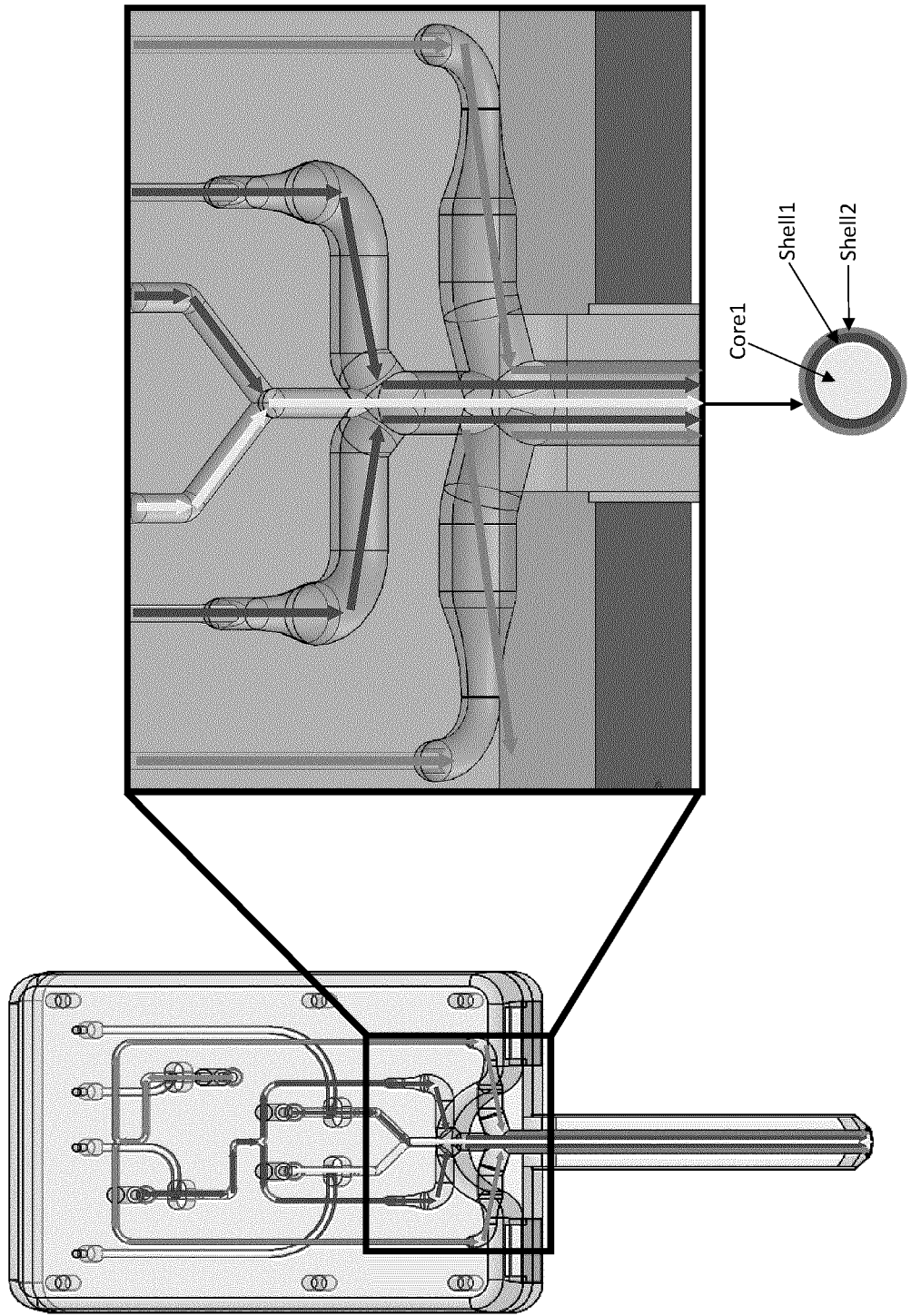
FIG. 1 is an illustration of the flow pattern in a horizontal embodiment of the inventive print head design.
Figure 2:
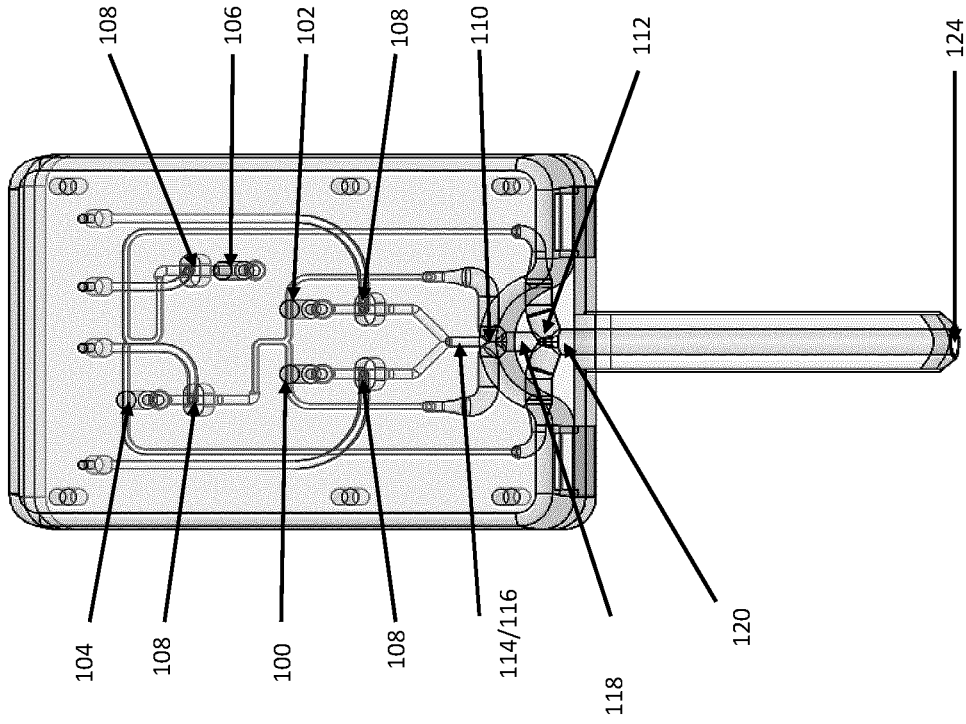
FIG. 2 illustrates and identifies key components of the microfluidic pathway in a horizontal embodiment of the inventive print head design.
Figure 3:
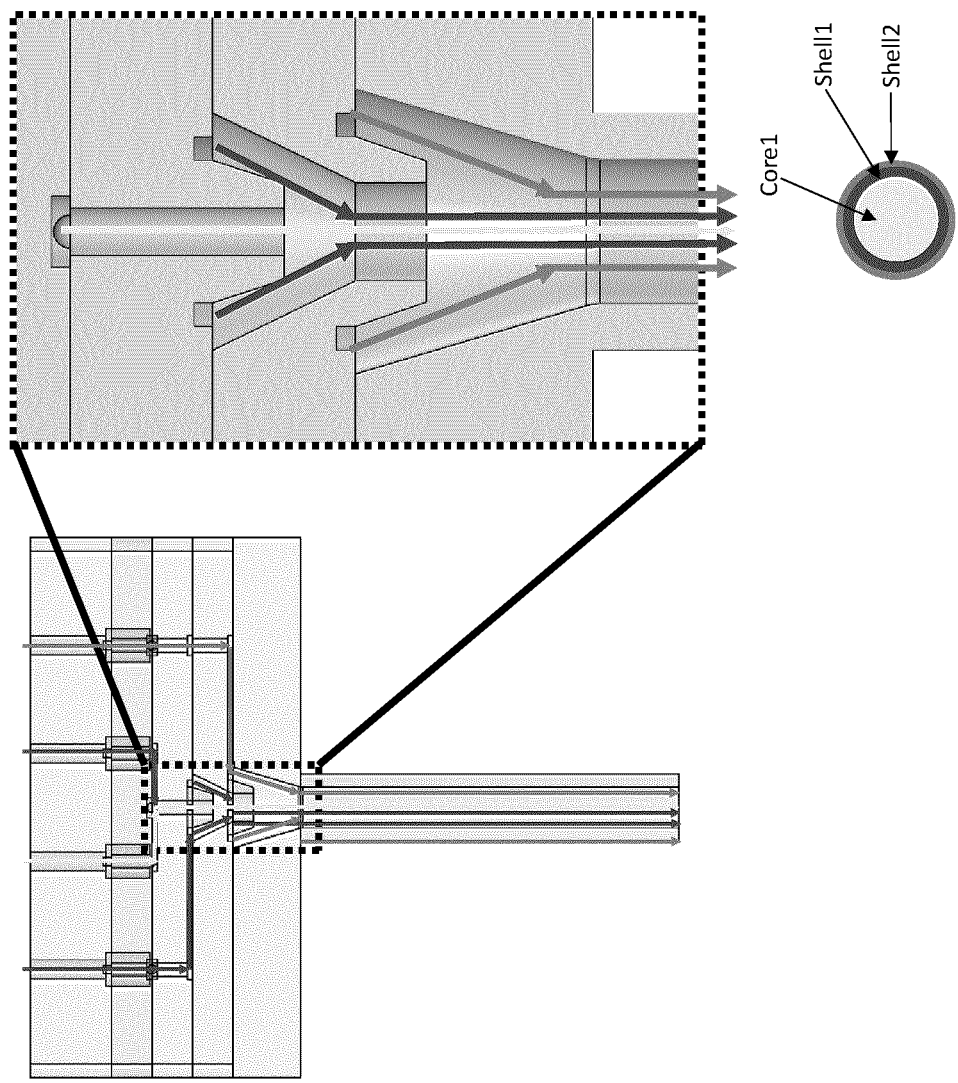
FIG. 3 is an illustration the flow pattern in a vertical embodiment of the inventive print head design.
Figure 4:
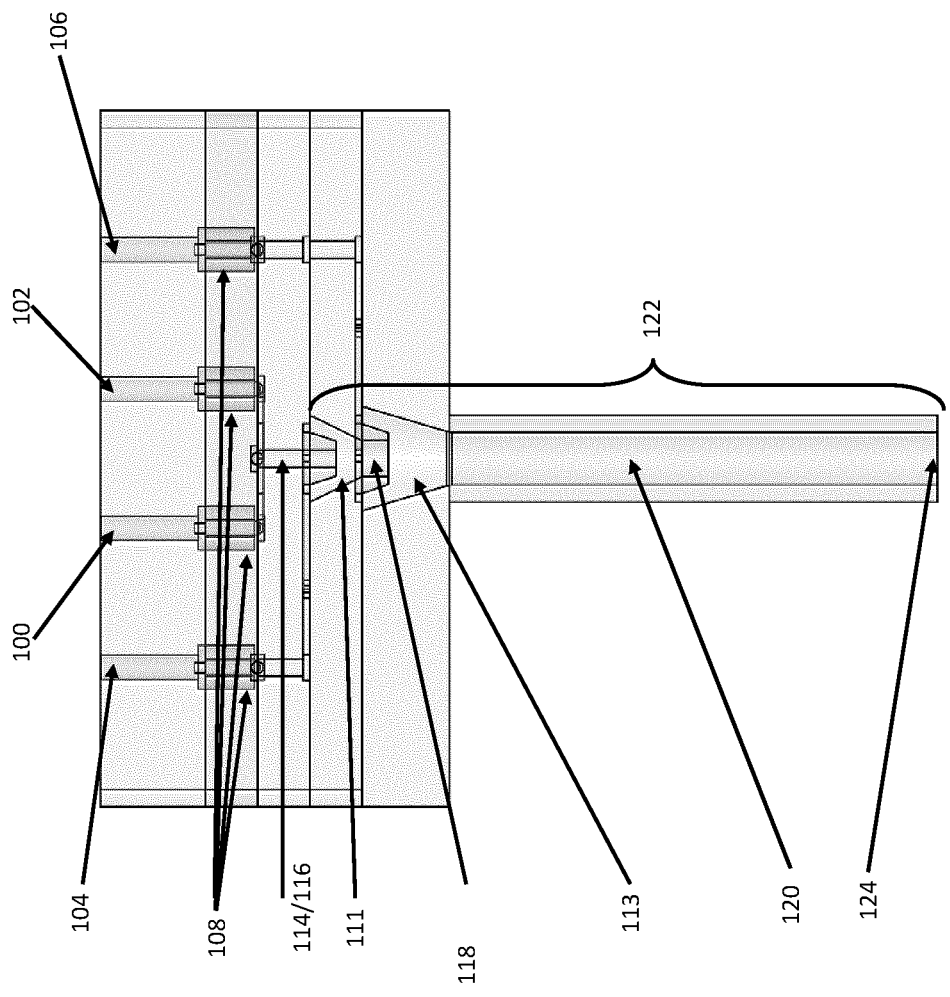
FIG. 4 illustrates and identifies key components of the microfluidic pathway in a vertical embodiment of the inventive print head design.
Figure 5:
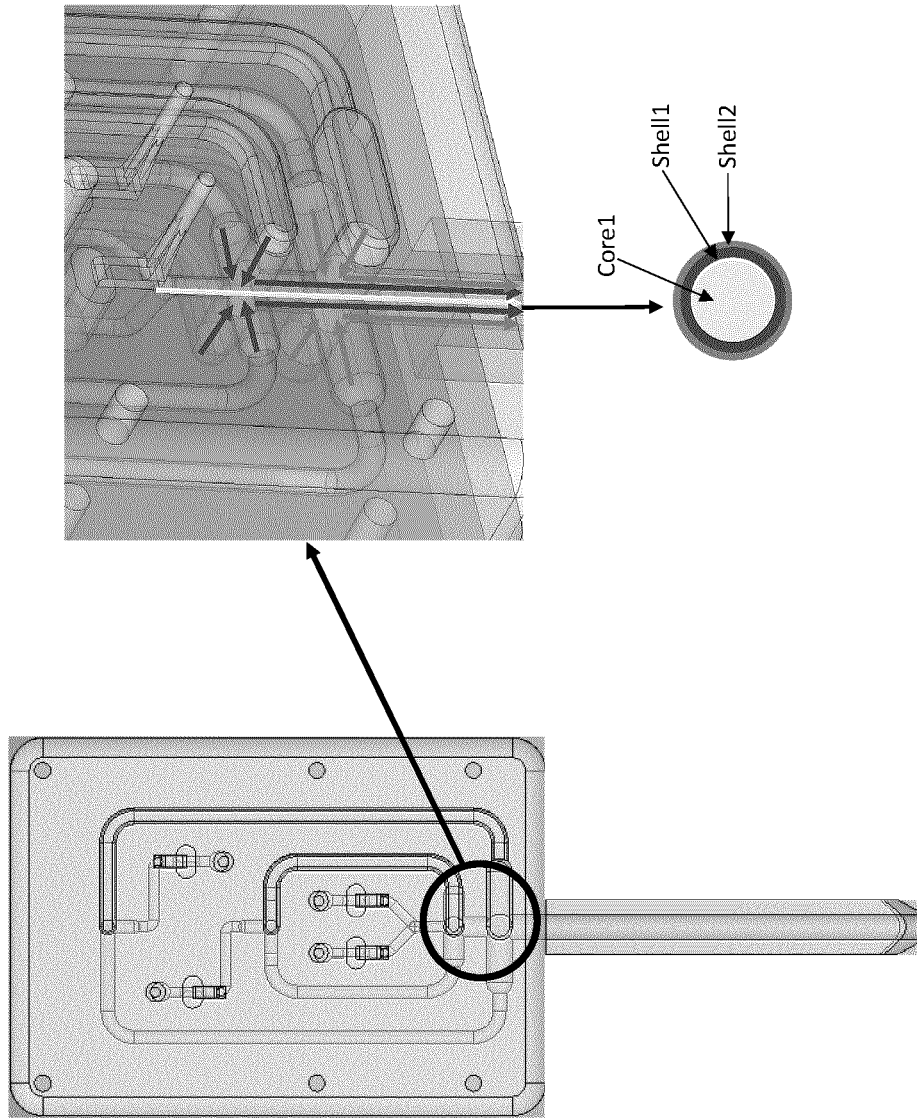
FIG. 5 is an illustration of the flow pattern in an alternative horizontal embodiment of the inventive print head design.
Figure 6:
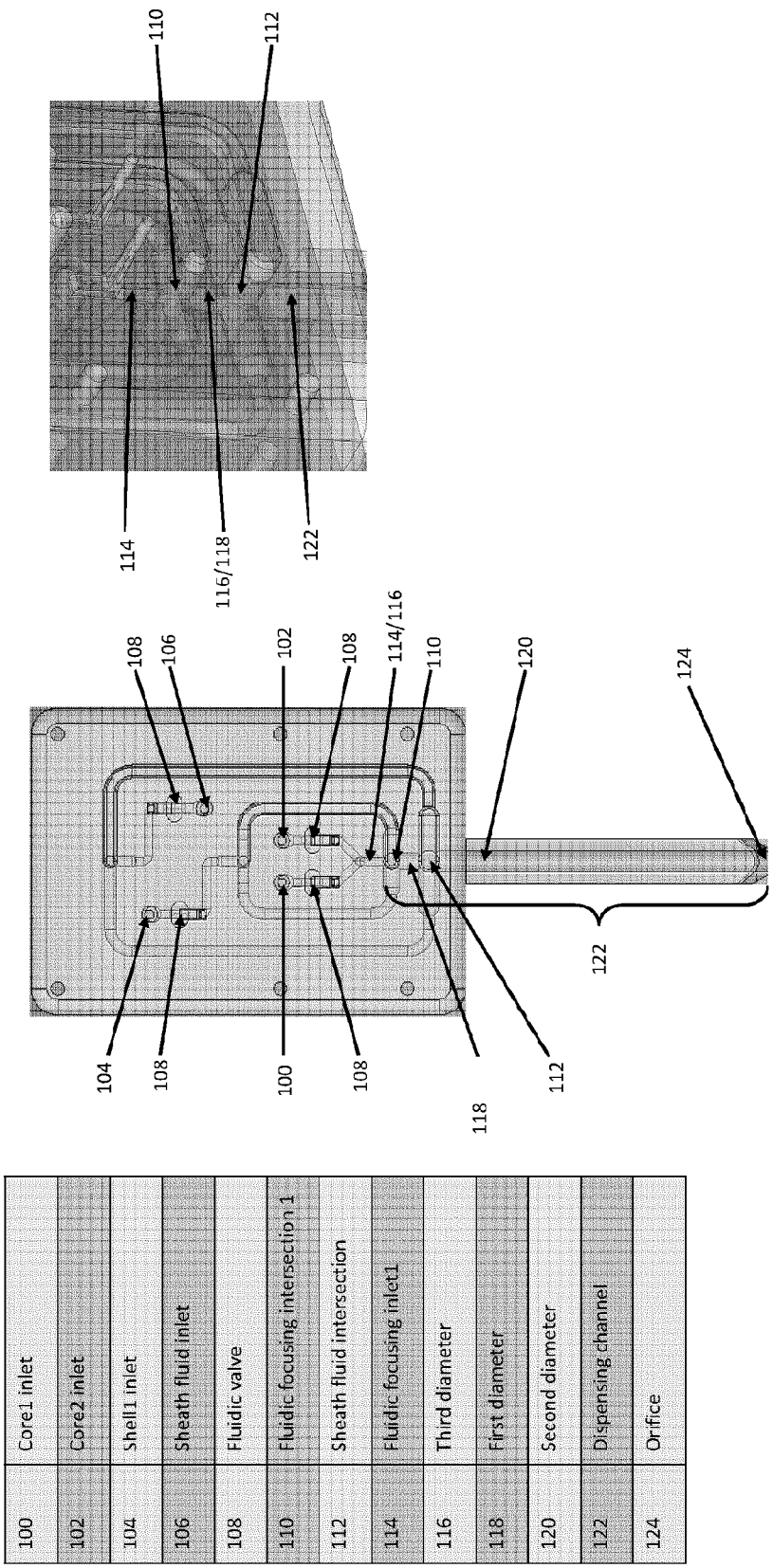
FIG. 6 illustrates and identifies key components of the microfluidic pathway in an alternative embodiment of the inventive print head design.
Figure 7:
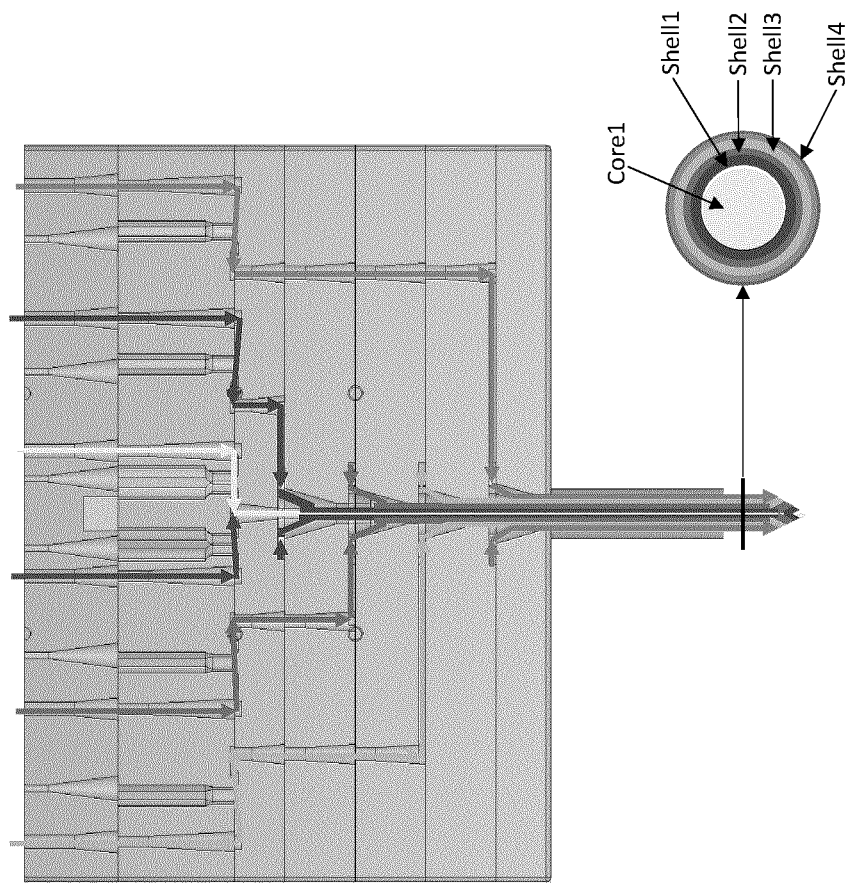
FIG. 7 is an illustration the flow pattern in an alternative vertical embodiment of the inventive print head design comprising multiple shell channels.
Figure 8:
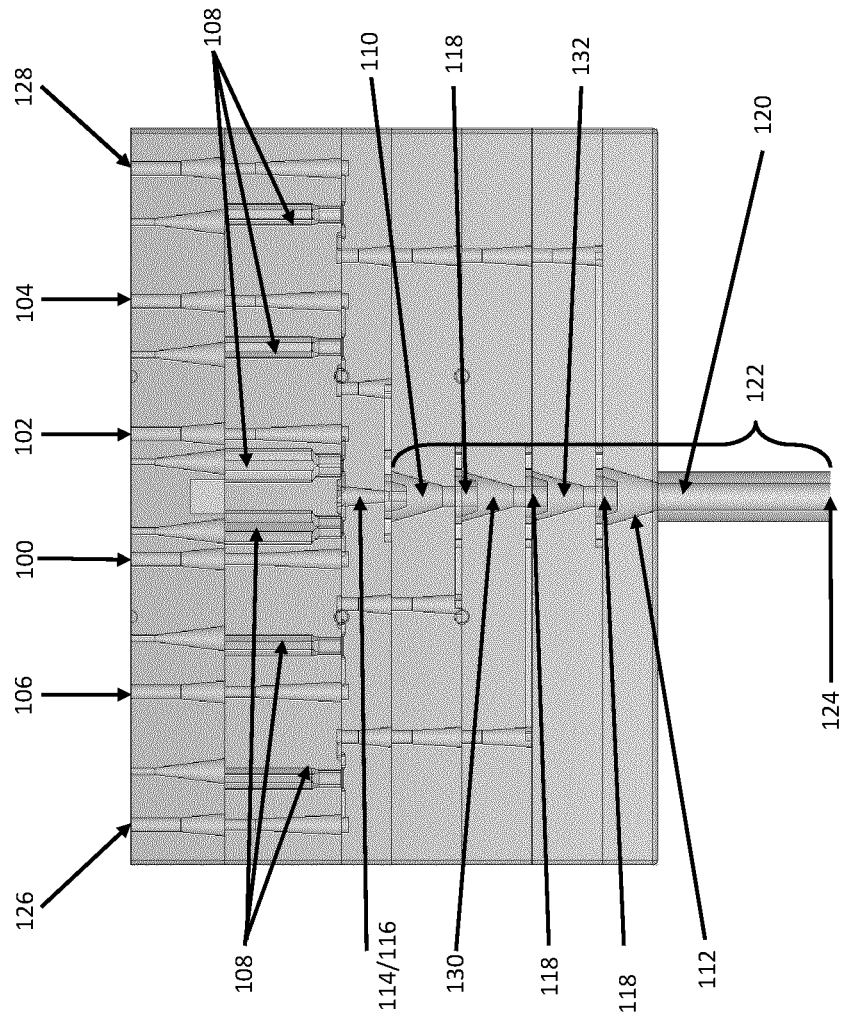
FIG. 8 illustrates and identifies key components of the microfluidic pathway in an alternative vertical embodiment of the inventive print head design comprising multiple shell channels.

D illustrates a large structure printed using a single continuous hollow fiber. The shell of the structure is transparent and the core is filled with a colored solution. E is a microscope image of a hollow fiber produced by an embodiment of the methods, compositions, and/or devices described herein. F is a microscope image of a solid fiber produced by an embodiment of the methods, compositions, and/or devices described herein.

DETAILED DESCRIPTION

Aspects of the invention include systems and methods for producing fiber structures, and for producing three-dimensional (3D) structures from digital files. In some embodiments, the printed fibers comprise living cells.

Definitions

For purposes of interpreting this specification, the following definitions will apply, and whenever appropriate, terms used in the singular will also include the plural and vice versa. In the event that any definition set forth conflicts with any document incorporated herein by reference, the definition set forth below shall control.

The term "displace" as used herein refers to the ability of a first material or fluid to remove a second material or fluid from a given position. For example, in some embodiments, a buffer solution is configured to displace an input material from a position within a dispensing channel (e.g., from a proximal end of the dispensing channel). In some embodiments, a displacement is an instantaneous displacement, which occurs in less than about one second, such as about 900, 800, 700, 600, 500, 400, 300, 200, or 100 milliseconds or less.

The term "miscible" as used herein refers to the ability of two different liquids to form a homogenous mixture when combined.

The term "mass flow rate" as used herein refers to the mass of a substance that passes a given position per unit of time. The term "constant mass flow rate" as used herein refers to a mass flow rate that remains constant per unit of time.

The term "solidified" as used herein refers to a solid or semi-solid state of material that maintains its shape fidelity and structural integrity upon deposition. The term "shape fidelity" as used herein means the ability of a material to maintain its three dimensional shape without significant spreading. In some embodiments, a solidified material is one having the ability to maintain its three dimensional shape for a period of time of about 30 seconds or more, such as about 1, 10 or 30 minutes or more, such as about 1, 10, 24, or 48 hours or more. The term "structural integrity" as used herein means the ability of a material to hold together under a load, including its own weight, while resisting breakage or bending.

In some embodiments, a solidified composition is one having an elastic modulus greater than about 5, 10, 15, 20 or 25 kilopascals (kPa), more preferably greater than about 30, 40, 50, 60, 70, 80 or 90 kPa, still more preferably greater than about 100, 110, 120 or 130 kPa. Preferred elastic modulus ranges include from about 5, 10, 15, 20, 25 or 50 Pa to about 80, 100, 120 or 140 kPa. According to the subject invention, the elastic modulus of an input material can be advantageously varied according to the intended function of the input material. In some embodiments, a lower elastic modulus is employed to support cell growth and migration, while in other embodiments, a much high elastic modulus can be used.

The term "native alginate polymer" as used herein refers to an alginate polymer that has been isolated and purified from one or more natural sources (e.g., one or more species of brown sea algae or seaweed).

The term "depolymerize" as used herein refers to breaking a polymer chain into monomers or other smaller units.

The term "hydrogel" as used herein refers to a composition comprising water and a network or lattice of polymer chains that are hydrophilic.

The term "sheath fluid" or "sheath solution" as used herein refers to a fluid that is used, at least in part, to envelope or "sheath" a material as the material is passing through a fluid channel. In some embodiments, a sheath fluid comprises an aqueous solvent, e.g., water or glycerol. In some embodiments, a sheath fluid comprises a chemical cross-linking agent. Non-limiting examples of crosslinking agents include divalent cations (e.g. Ca', Ba', Sr', etc.), thrombin, and pH modifying chemicals, such as sodium bicarbonate.

As used herein, the term "excess sheath fluid" refers to a portion of the sheath fluid that is dispensed from the dispensing orifice and does not form part of a fiber structure printed using one or more embodiments of the systems or methods provided herein. For example, the excess sheath fluid may be useful in lubricating passage of a material (e.g., a hydrogel) through a dispensing channel in the print head and through the dispensing orifice. Once dispensed from the dispensing orifice, the excess sheath fluid may run off of the surface of a layer of dispensed material and onto a receiving surface, where it may collect or pool.

The term "channel length" as used herein refers to the linear distance travelled when tracing a fluid channel from a first position to a second position.

The term "convergence angle" as used herein refers to an angle that is formed between two fluid channels that converge.

Print Heads:

Aspects of the invention include print heads that can be used to produce one or more hollow fiber structures. Print heads in accordance with embodiments of the invention comprise a plurality of interconnected fluid channels within a common housing or enclosure, and are configured to produce hollow fiber structures comprising one or more input materials. In some embodiments, a print head is configured to produce a solidified hollow fiber structure. In some embodiments, a print head is configured to produce a solidified hollow fiber structure comprising living cells.

In some embodiments, a print head comprises a dispensing channel having a distal end and a proximal end. Dispensing channels in accordance with embodiments of the invention can have a channel length that ranges from about 1 mm to about 100 mm, such as about 5, 10, 15, 20, 25, 30, 35, 40, 45, 50, 55, 60, 65, 70, 75, 80, 85, 90 or about 95 mm. Dispensing channels in accordance with embodiments of the invention can have a width or diameter that ranges from about 10 µm to about 5 mm, such as about 25, 50, 75 or 100 µm, or such as about 0.2, 0.3, 0.4, 0.5, 0.6, 0.7, 0.8, 0.9, 1.0, 2.0 or 3.0 mm. Dispensing channels in accordance with embodiments of the invention can have a depth that ranges from about 10 µm to about 5 mm, such as about 25, 50, 75 or 100 µm, or such as about 0.2, 0.3, 0.4, 0.5, 0.6, 0.7, 0.8, 0.9, 1.0, 2.0 or 3.0 mm. Dispensing channels in accordance with embodiments of the invention can have any suitable cross sectional shape, for example, a circular, oval, square or rectangular cross sectional shape.

In some embodiments, a dispensing channel comprises a dispensing orifice. In some embodiments, the dispensing orifice is located at the distal end of the dispensing channel. A dispensing orifice in accordance with embodiments of the invention can have a diameter that ranges from about 10 µm to about 5 mm, such as about 15, 20, 25, 30, 35, 40, 45, 50, 55, 60, 65, 70, 75, 80, 85, 90, 95 or 100 µm, or such as about 150, 200, 250, 300, 350, 400, 450, 500, 550, 600, 650, 700, 750, 800, 850, 900 or 950 µm. A dispensing orifice in accordance with embodiments of the invention can have any suitable cross sectional shape, for example, a circular, oval, square or rectangular cross sectional shape.

In some embodiments, a print head further comprises an extension tip comprising an orifice for dispensing materials from the print head. Such an extension tip facilitates precision dispensing of materials and deposition thereof in confined areas such as, for example, a well in a multi-well plate (e.g., a standard microtiter plate, multi-well plate or microplate having 6, 24, 96 or more wells) or a petri dish. In some embodiments, an extension tip comprises a tube (e.g., made of plastic, glass or metal) having an exterior configured to fit into a portion of the dispensing channel and an inner surface (defining a hollow space in the tube) configured to align with the dispensing channel. The extension tip can be inserted into the dispensing channel, thereby extending the length of the dispensing channel, which facilitates deposition of material dispensed from an orifice in the extension tip into confined spaces, such as a well plate insert or petri dish.

Print heads in accordance with embodiments of the invention comprise one or more core channels. In certain embodiments, the one or more core channels converge with the dispensing channel at the proximal end of the dispensing channel. In some embodiments, a core channel converges with the dispensing channel at a convergence angle that ranges from about 0 to about 180 degrees, such as about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, or 175 degrees. Core channels in accordance with embodiments of the invention can have any suitable channel length. In some embodiments, a core channel has a channel length that ranges from about 100 µm to about 100 mm, such as about 1, 2, 3, 4, 5, 6, 7, 8, 9, 10, 15, 20, 25, 30, 35, 40, 45, 50, 55, 60, 65, 70, 75, 80, 85, 90 or 95 mm. Core channels in accordance with embodiments of the invention can have a width or diameter that ranges from about 10 µm to about 5 mm, such as about 25, 50, 75 or 100 µm, or such as about 0.2, 0.3, 0.4, 0.5, 0.6, 0.7, 0.8, 0.9, 1.0, 2.0 or 3.0 mm. Material channels in accordance with embodiments of the invention can have a depth that ranges from about 10 µm to about 5 mm, such as about 25, 50, 75 or 100 µm, or such as about 0.2, 0.3, 0.4, 0.5, 0.6, 0.7, 0.8, 0.9, 1.0, 2.0 or 3.0 mm.

In some embodiments, a print head comprises at least two core sub-channels, which converge to form a first fluid focusing inlet having the third diameter. In some embodiments, a print head comprises a number of core sub-channels that ranges from 3 to 10, such as 4, 5, 6, 7, 8, or 9 material channels. Core channels in accordance with embodiments of the invention can have any suitable cross sectional shape, for example, a circular, oval, square or rectangular cross sectional shape. In some embodiments, the print head is configured to dispense non-cross-linkable materials through the core channel(s).

Print heads in accordance with embodiments of the invention comprise at least a first shell channel. In certain embodiments, the first shell channel converges with the core channel and the dispensing channel at the proximal end of the dispensing channel at a first fluidic focusing intersection. In some embodiments, the first shell channel converges with the dispensing channel at a convergence angle that ranges from about 0 to about 180 degrees, such as about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, or 175 degrees. Shell channels in accordance with embodiments of the invention can have any suitable length. In some embodiments, a shell channel has a channel length that ranges from about 100 µm to about 100 mm, such as about 1, 2, 3, 4, 5, 6, 7, 8, 9, 10, 15, 20, 25, 30, 35, 40, 45, 50, 55, 60, 65, 70, 75, 80, 85, 90 or 95 mm. Shell channels in accordance with embodiments of the invention can have a width or diameter that ranges from about 10 µm to about 5 mm, such as about 25, 50, 75 or 100 µm, or such as about 0.2, 0.3, 0.4, 0.5, 0.6, 0.7, 0.8, 0.9, 1.0, 2.0 or 3.0 mm. Shell channels in accordance with embodiments of the invention can have a depth that ranges from about 10 µm to about 5 mm, such as about 25, 50, 75 or 100 µm, or such as about 0.2, 0.3, 0.4, 0.5, 0.6, 0.7, 0.8, 0.9, 1.0, 2.0 or 3.0 mm. Shell channels in accordance with embodiments of the invention can have any suitable cross sectional shape, for example, a circular, oval, square or rectangular cross sectional shape.

Figure 9:
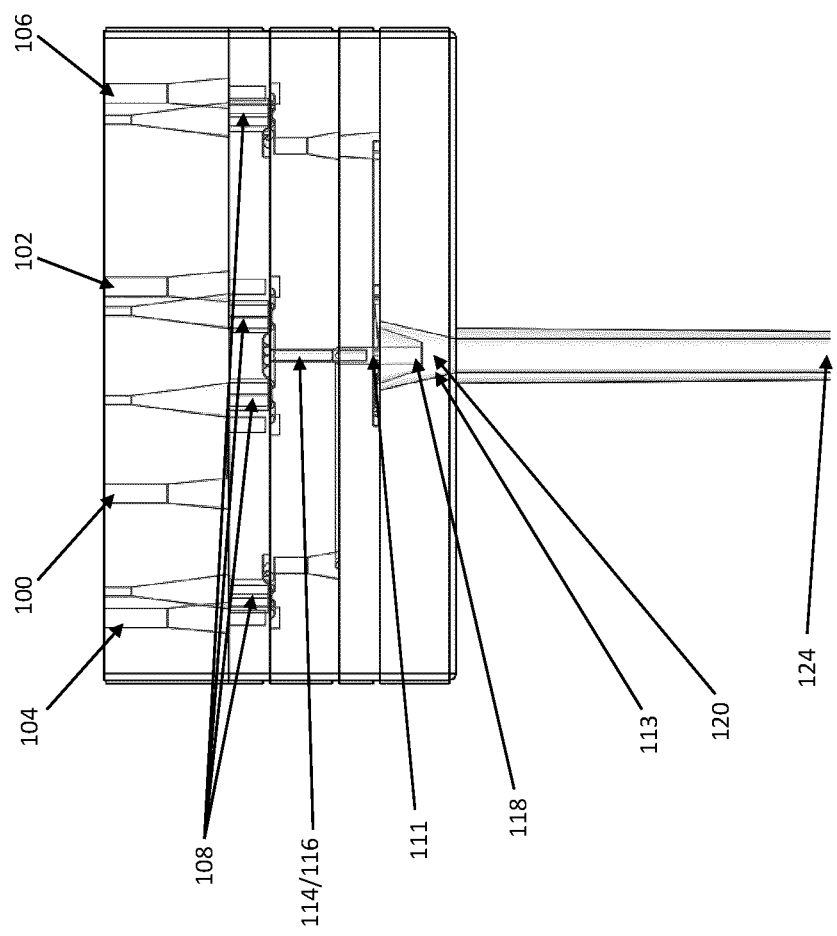
FIG. 9 illustrates and identifies key components of the microfluidic pathway in an alternative vertical embodiment of the inventive print head design comprising an embedded core shell channel.
Figure 10:
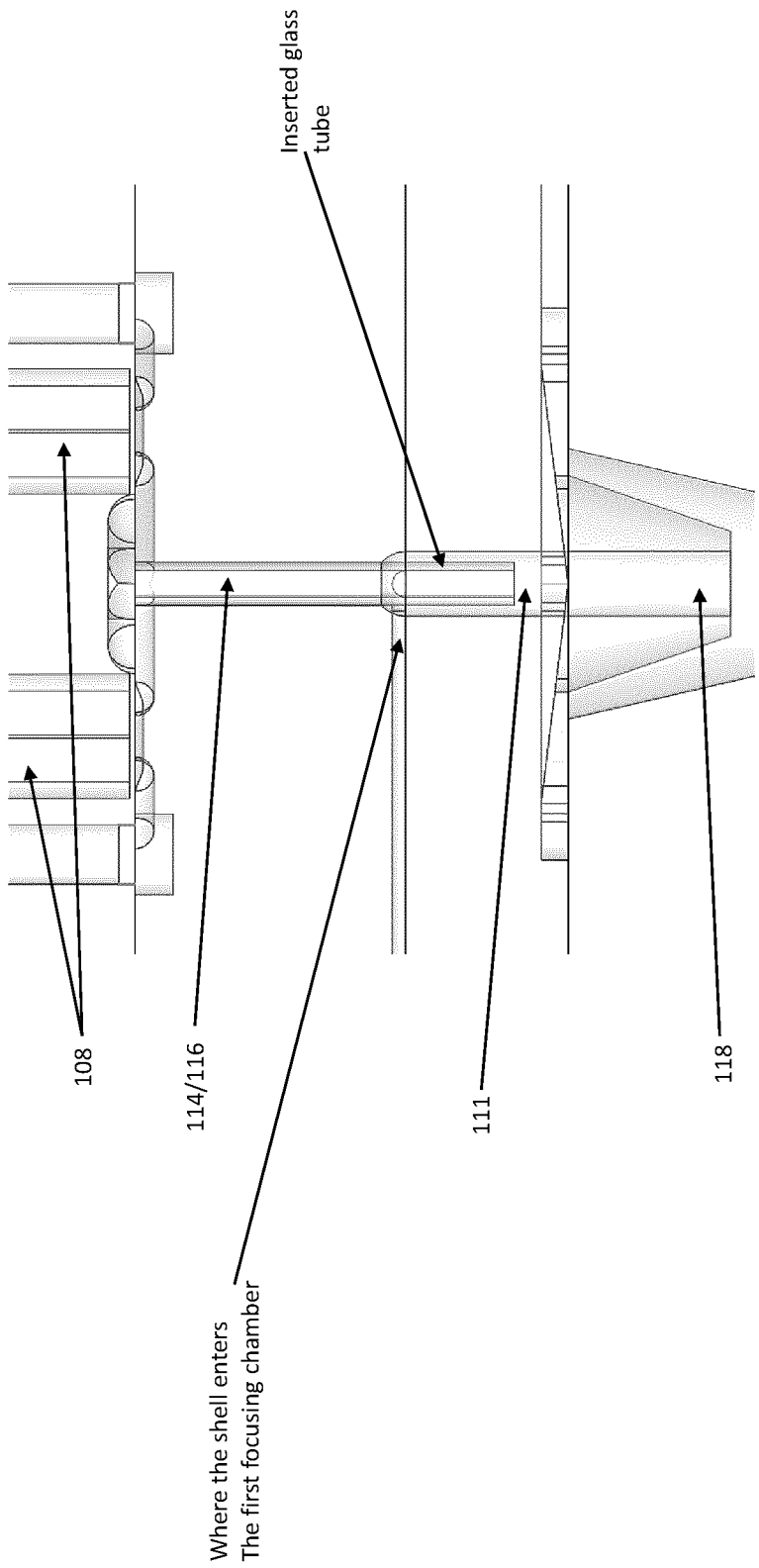
FIG. 10 illustrates an exploded view of the inventive print head design comprising an embedded core shell channel.
Figure 11:
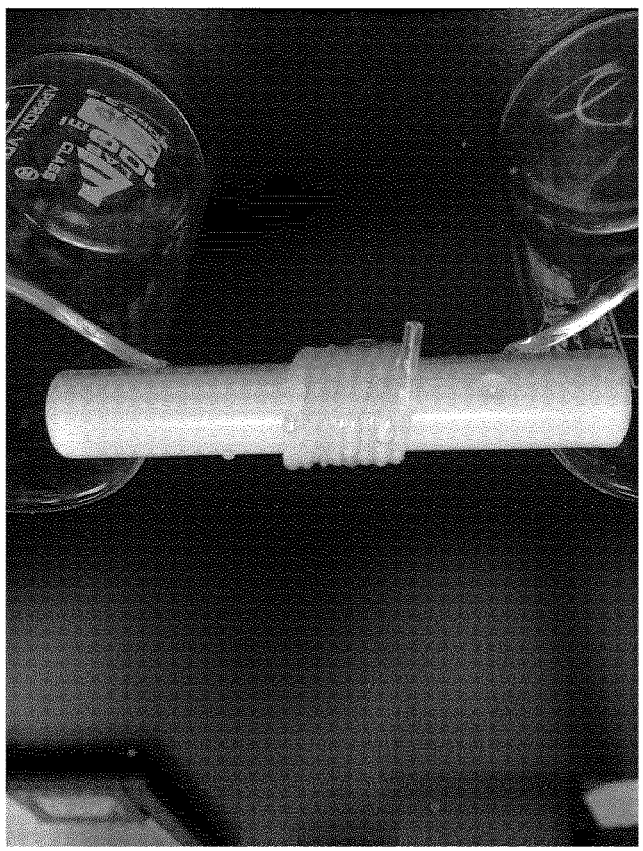
FIGS. 11A-F illustrate a hollow fiber produced by an embodiment of the methods, compositions, and/or devices described herein. A illustrates a hollow fiber wrapped around a mandrel. B illustrates a fluid-filled hollow fiber wrapped around a mandrel. C is an end view of a printed hollow fiber.
Figure 11:
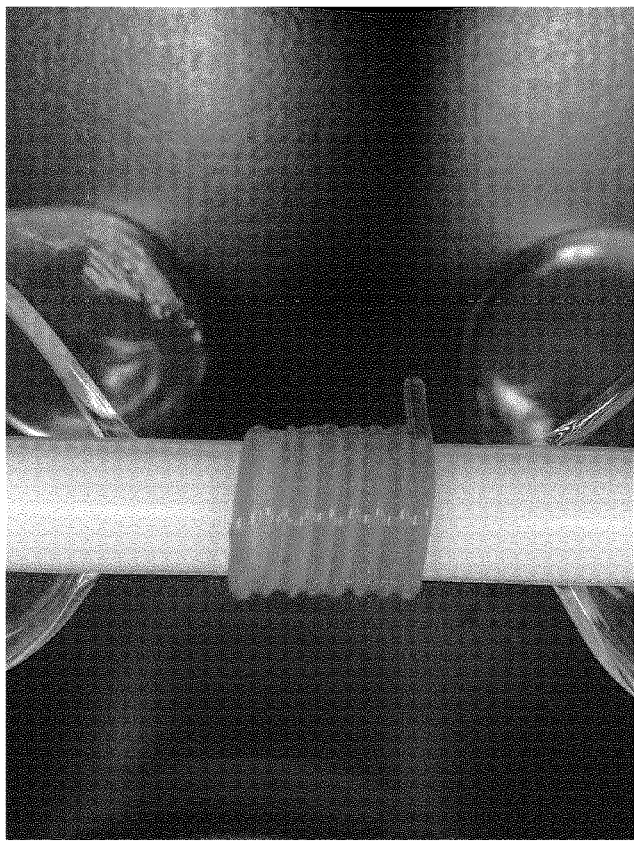
Figure 11:
Figure 11:
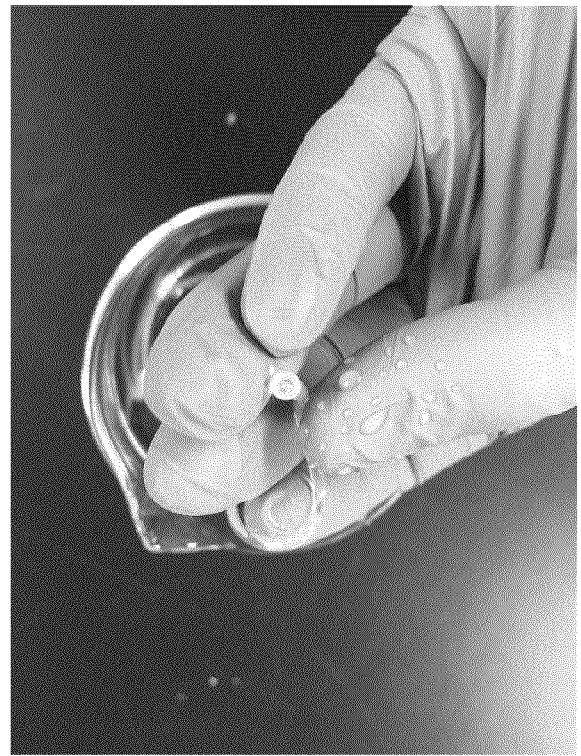
Figure 11:
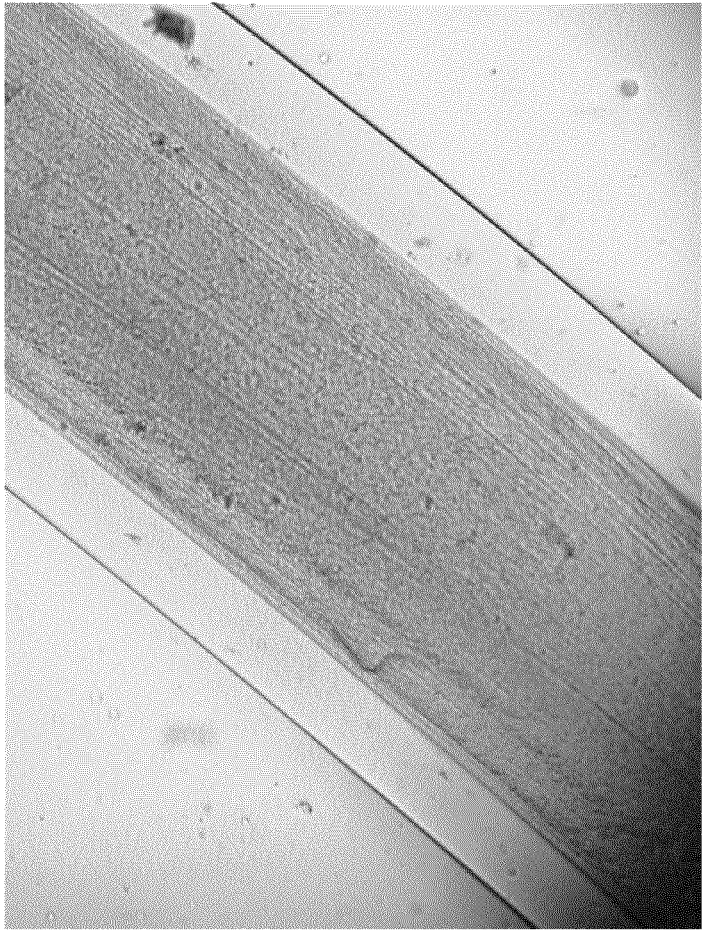
Figure 11:
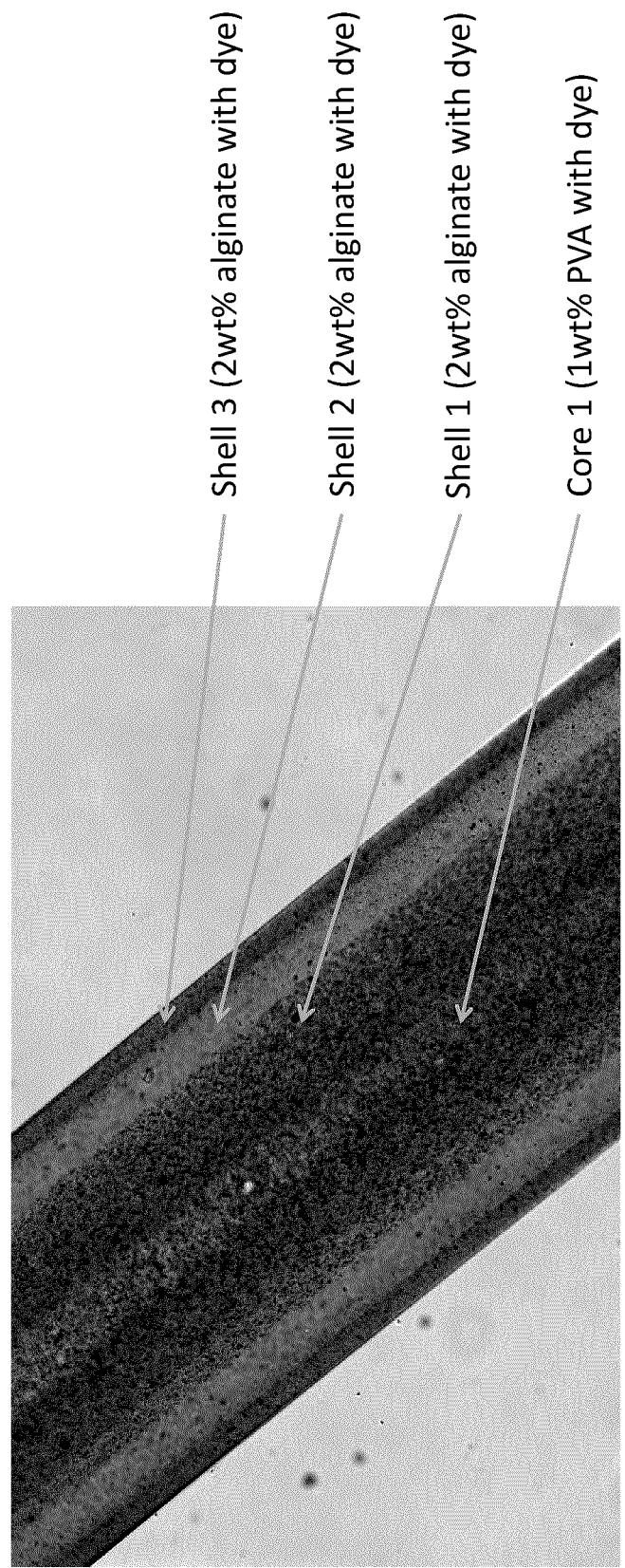

In certain embodiments, the first shell channel is concentrically disposed around the distal end of the core channel. In an exemplary embodiment, the distal end of the core channel comprises a tube disposed within the first shell channel in the print head, as shown in FIGS. 9 and 10. Suitable materials for such a tube include metal (e.g., stainless steel, brass, titanium, and Inconel), glass, fused silica, and plastic (e.g., polycarbonate, polyether ether ketone (PEEK), and polytetrafluoroethylene (PTFE)). In some embodiments, the distal end of the core channel comprises a tube having an exterior configured to fit into a portion of the first shell channel and an inner surface (defining a hollow space in the tube) configured to align with the core channel.

Print heads in accordance with embodiments of the invention comprise a sheath flow channel. In certain embodiments, the sheath flow channel converges with the dispensing channel at a sheath fluid intersection that is located between the first fluidic focusing intersection and the distal end of the dispensing channel. In some embodiments, a sheath flow channel converges with the dispensing channel at a convergence angle that ranges from about 0 to about 180 degrees, such as about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, or 175 degrees. In some embodiments, the distance between the proximal end of the dispensing channel and the sheath fluid intersection ranges from about 10 µm to about 100 mm, such as about 25, 50, 75 or 100 µm, or such as about 1, 5, 10, 15, 20, 25, 30, 35, 40, 45, 50, 55, 60, 65, 70, 75, 80, 85, 90 or 95 mm. In some embodiments, the distance between the distal end of the dispensing channel and the sheath fluid intersection ranges from about 10 µm to about 100 mm, such as about 25, 50, 75 or 100 µm, or such as about 1, 5, 10, 15, 20, 25, 30, 35, 40, 45, 50, 55, 60, 65, 70, 75, 80, 85, 90 or 95 mm.

Sheath flow channels in accordance with embodiments of the invention can have any suitable length. In some embodiments, a sheath flow channel has a channel length that ranges from about 100 µm to about 100 mm, such as about 1, 2, 3, 4, 5, 6, 7, 8, 9, 10, 15, 20, 25, 30, 35, 40, 45, 50, 55, 60, 65, 70, 75, 80, 85, 90 or 95 mm. Sheath flow channels in accordance with embodiments of the invention can have a width or diameter that ranges from about 10 μm to about 5 mm, such as about 25, 50, 75 or 100 μm, or such as about 0.2, 0.3, 0.4, 0.5, 0.6, 0.7, 0.8, 0.9, 1.0, 2.0 or 3.0 mm. Sheath flow channels in accordance with embodiments of the invention can have a depth that ranges from about 10 μm to about 5 mm, such as about 25, 50, 75 or 100 μm, or such as about 0.2, 0.3, 0.4, 0.5, 0.6, 0.7, 0.8, 0.9, 1.0, 2.0 or 3.0 mm. In some embodiments, a sheath flow channel comprises two or more sheath flow sub-channels. In some embodiments, the sheath flow channel diverges into a number of sheath flow sub-channels that ranges from 3 to 10, such as 4, 5, 6, 7, 8 or 9. In some embodiments, the two or more sheath flow sub-channels converge with the dispensing channel at the sheath fluid intersection. Sheath flow channels in accordance with embodiments of the invention can have any suitable cross sectional shape, for example, a circular, oval, square or rectangular cross sectional shape.

Fluid channels in accordance with embodiments of the invention generally include one or more input orifices, through which a fluid can be introduced into the channel. In some embodiments, a fluid channel comprises a control valve that is configured to modulate the flow of a fluid through the fluid channel. In some embodiments, a channel length between an input orifice and a control valve ranges from about 100 μm to about 100 mm, such as about 1, 2, 3, 4, 5, 6, 7, 8, 9, 10, 15, 20, 25, 30, 35, 40, 45, 50, 55, 60, 65, 70, 75, 80, 85, 90 or 95 mm. In some embodiments, a channel length between a control valve and a position where the channel converges with the dispensing channel ranges from about 100 μm to about 100 mm, such as about 1, 2, 3, 4, 5, 6, 7, 8, 9, 10, 15, 20, 25, 30, 35, 40, 45, 50, 55, 60, 65, 70, 75, 80, 85, 90 or 95 mm.

Print heads in accordance with embodiments of the invention can be made from any suitable material, including but not limited to plastic (e.g., a polymeric material), glass, metal, ceramic, or any combination thereof. In some embodiments, a print head comprises a material that is at least partially transparent to light (e.g., ultraviolet (UV) light). In some embodiments, a print head is made entirely of a transparent material. In certain embodiments, a portion of a print head that surrounds or is directly adjacent to a dispensing channel comprises a material that is partially or completely transparent to light. Such print heads can be used in conjunction with input materials that are configured to be crosslinked with light energy (e.g., photo crosslinkable input materials).

Aspects of the invention include light modules that are configured to expose a photo-crosslinkable input material to electromagnetic radiation in order to crosslink the input material. Light modules in accordance with embodiments of the invention can be integrated into a print head, or can be a separate component of a printing system. In some embodiments, a light module exposes an input material to light while the input material is within the dispensing channel. In some embodiments, a light module exposes an input material to light after the input material is dispensed from the dispensing channel. In some embodiments, a print head comprises a plurality of light modules, wherein a first light module is configured to expose an input material to light while the input material is within the dispensing channel, and a second light module is configured to expose an input material to light after the input material is dispensed from the dispensing channel.

In some embodiments, a light module is tunable with respect to wavelength, intensity, exposure time, or any combination thereof. In some embodiments, a light module comprises one or more optionally engaged attenuation filters, wherein the attenuation filters modulate light intensity when engaged. In some embodiments, a light module is configured to emit UV light, wherein the wavelength of light emitted from the module ranges from about 10 nm to about 400 nm, such as about 20, 30, 40, 50, 60, 70, 80, 90, 100, 125, 150, 175, 200, 225, 250, 275, 300, 325, 350 or 375 nm. In some embodiments, suitable sources of UV light include, by way of non-limiting examples, UV lamps, UV fluorescent lamps, UV LEDs, UV lasers, or any combination thereof.

As reviewed above, aspects of the invention include a print head comprising a dispensing channel, wherein one or more material channels and a buffer solution channel converge at the proximal end of the dispensing channel. The subject print heads are configured to dispense buffer solution and/or sheath fluid simultaneous with one or more cross-linkable materials so as to form a hollow core in the printed fiber. In some embodiments, a print head is configured to maintain a constant mass flow rate through the dispensing channel. In this manner, the subject print heads are configured to facilitate a smooth and continuous flow of one or more input materials (or a mixture of one or more input materials) and a buffer solution and/or sheath fluid through the dispensing channel.

As reviewed above, additional aspects of the invention include a print head comprising a dispensing channel, wherein one or more sheath flow channels converge with the dispensing channel at a sheath fluid intersection that is located between the first fluidic focusing intersection and the distal end of the dispensing channel. In use of the subject print heads, an input material flowing through the dispensing channel can be cross-linked both from the inside, by sheath fluid flowing through the core channel, as well as from the outside, by sheath fluid flowing through the sheath flow channel.

In a preferred embodiment, a print head comprises a dispensing channel with a proximal end and a distal end; a dispensing orifice located at the distal end of the dispensing channel; two shell channels that converge with the dispensing channel at the distal end of the dispensing channel, wherein each shell channel has a convergence angle of between about 30 and 60 degrees, more preferably between about 40 and 50 degrees, and most preferably about 45 degrees; a core channel that converges with the dispensing channel at the proximal end of the dispensing channel, wherein the core channel has a convergence angle of 0 degrees; and a sheath flow channel that diverges into two sheath flow sub-channels, wherein the sheath flow sub-channels converge with the dispensing channel at a sheath fluid intersection and have a convergence angle of between about 30 and 60 degrees, more preferably between about 40 and 50 degrees, most preferably about 45 degrees.

In another preferred embodiment, a print head comprises a dispensing channel with a proximal end and a distal end; a dispensing orifice located at the distal end of the dispensing channel; four shell channels that converge with the dispensing channel at the distal end of the dispensing channel, wherein each shell channel has a convergence angle of between about 20 and 90 degrees, a core channel that converges with the dispensing channel at the proximal end of the dispensing channel, wherein the core channel has a convergence angle of 0 degrees; and a sheath flow channel that diverges into two sheath flow sub-channels, wherein the sheath flow sub-channels converge with the dispensing channel at a sheath fluid intersection and have a convergence angle of between about 30 and 60 degrees, more preferably between about 40 and 50 degrees, most preferably about 45 degrees.

Printing Systems:

Aspects of the invention include printing systems and associated components that are configured to work in conjunction with the subject print heads to carry out the subject methods. In some embodiments, a printing system comprises a single print head, as described herein. In some embodiments, a printing system comprises a plurality of print heads, such as 2, 3, 4, 5, 6, 7, 8, 9 or 10 individual print heads, as described herein. In some embodiments, a print head is fluidically isolated from a printing system, such that all fluids involved with the printing process remain isolated within the print head, and only make contact with a receiving surface of the printing system (described below) during the printing process. In some embodiments, a print head is configured to be operably coupled to a printing system without bringing the fluids involved with the printing process into contact with the components of the printing system. In some embodiments, one or more print heads can be removed and/or added to a printing system before, during and/or after a printing process. Accordingly, in some embodiments, the subject print heads are modular components of the subject printing systems.

In some embodiments, a printing system comprises a receiving surface upon which a first layer of material dispensed from a dispensing orifice of a print head is deposited. In some embodiments, a receiving surface comprises a solid material. In some embodiments, a receiving surface comprises a porous material. For example, in some embodiments, the porosity of the porous material is sufficient to allow passage of a fluid there through. In some embodiments, a receiving surface is substantially planar, thereby providing a flat surface upon which a first layer of dispensed material can be deposited. In some embodiments, a receiving surface has a topography that corresponds to a three dimensional structure to be printed, thereby facilitating printing of a three dimensional structure having a non-planar first layer.

In some embodiments, a receiving surface comprises a vacuum component that is configured to apply suction from one or more vacuum sources to the receiving surface. In some embodiments, a receiving surface comprises one or more vacuum channels that are configured to apply suction to the receiving surface. In some embodiments, a receiving surface comprising a vacuum component is configured to aspirate an excess fluid from the receiving surface before, during and/or after a printing process is carried out.

In some embodiments, a receiving surface is a non-cytotoxic surface onto which a printing system dispenses one or more fiber structures. In some embodiments, a printing system comprises a printer stage. In some embodiments, a receiving surface is a surface of a printer stage. In some embodiments, a receiving surface is a component that is separate from a printer stage, but is affixed to or supported by a printer stage. In some embodiments, a receiving surface is flat or substantially flat. In some embodiments, a receiving surface is smooth or substantially smooth. In some embodiments, a receiving surface is both substantially flat and substantially smooth. In some embodiments, a receiving surface is configured to accommodate the shape, size, texture, or geometry of a printed structure. In some embodiments, a receiving surface controls or influences the size, shape, texture, or geometry of a printed structure.

In some embodiments, a receiving surface comprises one or more modular components that are configured to be operably coupled to a printing system, but which are separable from the printing system. In some embodiments, a receiving surface is a disposable receiving surface. In some embodiments, a receiving surface is configured for sterilization. In some embodiments, an entire fluid path of a printing system is disposable, meaning that all components of the printing system that come into contact with one or more fluids involved with the printing process are disposable, and can be removed from the printing system and exchanged for clean components.

In some embodiments, a receiving surface is configured to be operably coupled to one or more different receiving vessels. For example, in some embodiments, a receiving surface comprises a circular portion that is sized to be operably coupled to a circular receiving vessel (e.g., a petri dish). In some embodiments, a receiving surface comprises a square or rectangular portion that is sized to be operably coupled to a square or rectangular receiving vessel (e.g., a multi-well plate (e.g., a 6-well plate)). Receiving surfaces in accordance with embodiments of the invention can have any suitable size or geometry to accommodate a suitable receiving vessel.

In some embodiments, a printing system comprises a temperature modulation component that is configured to modulate the temperature of a receiving surface. In some embodiments, the temperature modulation component adjusts and/or maintains the temperature of the receiving surface to ambient temperature. In some embodiments, the temperature modulation component adjusts and/or maintains the temperature of a print head, a printer stage, a receiving surface, an input material, and/or a fluid (e.g., a sheath solution and/or a buffer solution).

In some embodiments, a temperature modulation component comprises a heating element. In some embodiments, a temperature modulation component comprises a heater. In some embodiments, a temperature modulation component comprises a radiant heater, a convection heater, a conductive heater, a fan heater, a heat exchanger, or any combination thereof. In some embodiments, a temperature modulation component comprises a cooling element. In some embodiments, a temperature modulation component comprises a container of coolant, a chilled liquid, ice, or any combination thereof. In some embodiments, a temperature modulation component comprises a radiant cooler, a convection cooler, a conductive cooler, a fan cooler, or any combination thereof.

In some embodiments, a temperature modulation component is configured to adjust a temperature to a set point that ranges from about 0 to about 90° C., such as about 1, 2, 3, 4, 5, 10, 15, 20, 25, 30, 35, 40, 45, 50, 55, 60, 65, 70, 75, 80 or 85° C.

In some embodiments, a printing system achieves a particular geometry by moving a print head relative to a printer stage or receiving surface adapted to receive printed materials. In other embodiments, a printing system achieves a particular geometry by moving a printer stage or receiving surface relative to a print head. In certain embodiments, at least a portion of a printing system is maintained in a sterile environment (e.g., within a biosafety cabinet (BSC)). In some embodiments, a printing system is configured to fit entirely within a sterile environment.

In some embodiments, a receiving surface receives excess fluid (e.g., excess sheath fluid and/or excess buffer solution) that is dispensed from the dispensing orifice, and that runs off of one or more layers of material dispensed from the dispensing orifice.

In some embodiments, a system comprises a component for removing excess fluid (e.g., excess sheath fluid and/or excess buffer solution) from a receiving surface where a fiber structure dispensed from the orifice of the print head is deposited, and optionally from a surface of a dispensed fiber structure. During printing, it is possible that excess fluid will collect or "pool" on the receiving surface or on a surface of dispensed fiber structure. Such pooling can interfere with the deposition process. For example, pooled sheath fluid may cause a dispensed fiber to slip from its intended position in a 3D structure being printed. Therefore, in some embodiments, removal of excess sheath fluid from the receiving surface and optionally from a surface of the dispensed fiber structure by way of a fluidic removal component may improve additive manufacturing of three-dimensional structures.

Excess fluid may be removed from the receiving surface or from a surface of one or more layers of dispensed fibers by drawing the fluid off of those surfaces, by allowing or facilitating evaporation of the fluid from those surfaces or, in embodiments where the receiving surface is porous, excess fluid may be removed by drawing it through the porous surface. In some embodiments, a receiving surface comprises a porous material, the pores being sized to facilitate passage of fluid there through, and sized to support one or more layers of fiber structures deposited thereon.

In some embodiments, a component for removing excess fluid from the receiving surface, and optionally from a surface of dispensed fiber structure, can be included in a system configured to dispense materials into a multiwall plate or petri dish. In some embodiments, the receiving surface on the print bed comprises or is placed adjacent to an absorptive material, which facilitates absorption of excess fluid from the receiving surface. For example, a well-plate insert having a base made out of a porous membrane material, or any other porous membrane substrate, can be placed on top of or adjacent to an absorptive material, such as, for example, a sponge. The absorptive material acts to draw excess fluid away from the receiving surface. In embodiments where the absorbent material is disposed below a porous receiving surface, excess fluid on the receiving surface can be drawn through the porous receiving surface and into the absorptive material, thereby preventing pooling of excess fluid on the receiving surface. In embodiments where the absorbent material is disposed immediately beside or on top of a portion of the receiving surface (e.g., on the periphery of the receiving surface so as not to interfere with deposition of dispensed material), excess sheath fluid can be drawn off of the receiving surface and into the absorbent material.

In some embodiments, a receiving surface comprises one or more tubes that are fluidly coupled to a vacuum source, which can provide suction for removing excess fluid from the receiving surface, and optionally from a surface of dispensed fiber structure. In such embodiments, a solid or porous receiving surface can also be used. In some embodiments, a print head is configured to further comprise one or more vacuum channels, the one or more vacuum channels each having an orifice situated near (i.e., adjacent to) the dispensing orifice. The one or more vacuum channels each have an inlet configured to facilitate fluid communication with one or more vacuums. When the print head is in fluid communication with a vacuum, the one or more vacuum channels direct negative pressure to an area of the receiving surface where materials are being dispensed or have been dispensed from the dispensing orifice and/or to a portion of the surface area of the dispensed fiber structure, thereby drawing up excess fluid from the receiving surface and optionally from a surface of the dispensed fiber structure, thereby eliminating pooling of fluid on the receiving surface and/or the dispensed fiber structure.

In some embodiments, the one or more vacuum tubes are provided, at least in part, in one or more extensions projecting from the print head, the extensions projecting in the same general direction as the extension comprising the dispensing orifice and dispensing channel. In such embodiments, the one or more extensions comprising vacuum tubes do not extend further than the extension comprising the dispensing orifice and dispensing channel so as not to interfere with the dispensing process.

In some embodiments, a fluid removal feature can be a feature of the fluid composition itself. For example, a sheath fluid composition and/or a buffer solution composition can be designed to evaporate after it is dispensed from the dispensing orifice, thereby eliminating pooling of excess fluid on the receiving surface or on surfaces of dispensed fiber structures. For example, the sheath fluid can have a boiling point that results in evaporation after being dispensed, while remaining in a liquid state prior to being dispensed.

In some embodiments, a printing system comprises a 3D motorized stage comprising three arms for positioning a print head and a dispensing orifice in three dimensional space above a print bed, which comprises a surface for receiving a printed material. In one embodiment, the 3D motorized stage (i.e., the positioning unit) can be controlled to position a vertical arm, which extends along the z-axis of the 3D motorized stage such that the print head orifice is directed downward. A first horizontal arm, which extends along the x-axis of the motorized stage is secured to an immobile base platform. A second horizontal arm, which extends along the y-axis of the motorized stage is moveably coupled to an upper surface of the first horizontal arm such that the longitudinal directions of the first and second horizontal arms are perpendicular to one another. It will be understood that the terms "vertical" and "horizontal" as used above with respect to the arms are meant to describe the manner in which the print head is moved and do not necessarily limit the physical orientation of the arms themselves.

In some embodiments, a receiving surface is positioned on top of a platform, the platform being coupled to an upper surface of the second horizontal arm. In some embodiments, the 3D motorized stage arms are driven by three corresponding motors, respectively, and controlled by a programmable control processor, such as a computer. In a preferred embodiment, a print head and a receiving surface are collectively moveable along all three primary axes of a Cartesian coordinate system by the 3D motorized stage, and movement of the stage is defined using computer software. It will be understood that the invention is not limited to only the described positioning system, and that other positioning systems are known in the art. As material is dispensed from a dispensing orifice on a print head, the positioning unit is moved in a pattern controlled by software, thereby creating a first layer of the dispensed material on the receiving surface. Additional layers of dispensed material are then stacked on top of one another such that the final 3D geometry of the dispensed layers of material is generally a replica of a 3D geometry design provided by the software. The 3D design may be created using typical 3D CAD (computer aided design) software or generated from digital images, as known in the art. Further, if the software generated geometry contains information on specific materials to be used, it is possible, according to one embodiment of the invention, to assign a specific input material type to different geometrical locations. For example, in some embodiments, a printed 3D structure can comprise two or more different input materials, wherein each input material has different properties (e.g., each input material comprises a different cell type, a different cell concentration, a different ECM composition, etc.).

Aspects of the subject printing systems include software programs that are configured to facilitate deposition of the subject input materials in a specific pattern and at specific positions in order to form a specific fiber, planar or 3D structure. In order to fabricate such structures, the subject printing systems deposit the subject input materials at precise locations (in two or three dimensions) on a receiving surface. In some embodiments, the locations at which a printing system deposits a material are defined by a user input, and are translated into computer code. In some embodiments, a computer code includes a sequence of instructions, executable in the central processing unit (CPU) of a digital processing device, written to perform a specified task. In some embodiments, printing parameters including, but not limited to, printed fiber dimensions, pump speed, movement speed of the print head positioning system, and crosslinking agent intensity or concentration are defined by user inputs and are translated into computer code. In some embodiments, printing parameters are not directly defined by user input, but are derived from other parameters and conditions by the computer code.

Aspects of the present invention include methods for fabricating tissue constructs, tissues, and organs, comprising: a computer module receiving input of a visual representation of a desired tissue construct; a computer module generating a series of commands, wherein the commands are based on the visual representation and are readable by a subject printing system; a computer module providing the series of commands to a printing system; and the printing system depositing one or more input materials according to the commands to form a construct with a defined geometry.

In some embodiments, the locations at which a printing system deposits an input material are defined by a user input and are translated into computer code. In some embodiments, the devices, systems, and methods disclosed herein further comprise non-transitory computer readable storage media or storage media encoded with computer readable program code. In some embodiments, a computer readable storage medium is a tangible component of a digital processing device such as a bioprinter (or a component thereof) or a computer connected to a bioprinter (or a component thereof). In some embodiments, a computer readable storage medium is optionally removable from a digital processing device. In some embodiments, a computer readable storage medium includes, by way of non-limiting example, a CD-ROM, DVD, flash memory device, solid state memory, magnetic disk drive, magnetic tape drive, optical disk drive, cloud computing system and/or service, and the like. In some cases, the program and instructions are permanently, substantially permanently, semi-permanently, or non-transitorily encoded on a storage medium.

In some embodiments, the devices, systems, and methods described herein comprise software, server, and database modules. In some embodiments, a "computer module" is a software component (including a section of code) that interacts with a larger computer system. In some embodiments, a software module (or program module) comes in the form of one or more files and typically handles a specific task within a larger software system.

In some embodiments, a module is included in one or more software systems. In some embodiments, a module is integrated with one or more other modules into one or more software systems. A computer module is optionally a stand-alone section of code or, optionally, code that is not separately identifiable. In some embodiments, the modules are in a single application. In other embodiments, the modules are in a plurality of applications. In some embodiments, the modules are hosted on one machine. In some embodiments, the modules are hosted on a plurality of machines. In some embodiments, the modules are hosted on a plurality of machines in one location. In some embodiments, the modules are hosted a plurality of machines in more than one location. Computer modules in accordance with embodiments of the invention allow an end user to use a computer to perform the one or more aspects of the methods described herein.

In some embodiments, a computer module comprises a graphical user interface (GUI). As used herein, "graphic user interface" means a user environment that uses pictorial as well as textual representations of the input and output of applications and the hierarchical or other data structure in which information is stored. In some embodiments, a computer module comprises a display screen. In further embodiments, a computer module presents, via a display screen, a two-dimensional GUI. In some embodiments, a computer module presents, via a display screen, a three-dimensional GUI such as a virtual reality environment. In some embodiments, the display screen is a touchscreen and presents an interactive GUI.

Aspects of the invention include one or more quality control components that are configured to monitor and/or regulate one or more parameters of the subject printing systems in order to ensure that one or more printed fibers have suitable properties. For example, in some embodiments, if a deposition process proceeds too quickly, a printed fiber structure can begin to form a coiled structure within the dispensing channel or outside the dispensing channel after it has been dispensed. In some embodiments, a quality control component comprises a camera that is configured to monitor the deposition process by collecting one or more images of a printed fiber structure, and to determine whether the printed fiber structure has formed a coiled structure. In some embodiments, a quality control component is configured to modulate one or more parameters of a deposition process (e.g., to reduce pressure and/or to reduce deposition speed) so as to diminish or avoid formation of a coiled structure by the printed fiber structure.

Aspects of the invention include one or more fluid reservoirs that are configured to store a fluid and deliver the fluid to the printing system (e.g., the print head) through one or more fluid channels, which provide fluid communication between the printing system and the reservoirs. In some embodiments, a printing system comprises one or more fluid reservoirs that are in fluid communication with a fluid channel. In some embodiments, a fluid reservoir is connected to an input orifice of a fluid channel. In some embodiments, a fluid reservoir is configured to hold a volume of fluid that ranges from about 100 µL up to about 1 L, such as about 1, 5, 10, 15, 20, 25, 30, 35, 40, 45, 50, 55, 60, 65, 70, 75, 80, 85, 90, 95 or 100 mL, or such as about 150, 200, 250, 300, 350, 400, 450, 500, 550, 600, 650, 700, 750, 800, 850, 900 or 950 mL.

In some embodiments, a printing system comprises a pressure control unit, which is fluidly coupled to the one or more reservoirs. The pressure control unit is configured to provide a force to move one or more fluids through the printing system. In some embodiments, a pressure control unit supplies pneumatic pressure to one or more fluids via one or more connecting tubes. The pressure applied forces a fluid out of a reservoir and into the print head via respective fluid channels. In some embodiments, alternative means can be used to move a fluid through a channel. For example, a series of electronically controlled syringe pumps could be used to provide force for moving a fluid through a print head.

In some embodiments, a printing system comprises a light module (as described above) for optionally exposing a photo crosslinkable input material to light in order to crosslink the material. Light modules in accordance with embodiments of the invention can be integrated into a print head, or can be a component of a printing system.

Input Materials:

Aspects of the invention include input materials that can be used for printing fiber structures. In some embodiments, an input material comprises a hydrogel. Non-limiting examples of hydrogels include alginate, agarose, collagen, fibrinogen, gelatin, chitosan, hyaluronic acid based gels, or any combination thereof. A variety of synthetic hydrogels are known and can be used in embodiments of the systems and methods provided herein. For example, in some embodiments, one or more hydrogels form the structural basis for three dimensional structures that are printed. In some embodiments, a hydrogel has the capacity to support growth and/or proliferation of one or more cell types, which may be dispersed within the hydrogel or added to the hydrogel after it has been printed in a three dimensional configuration. In some embodiments, a hydrogel is cross-linkable by a chemical cross-linking agent. For example, a hydrogel comprising alginate may be cross-linkable in the presence of a divalent cation, a hydrogel containing chitosan may be cross-linked using a polyvalent anion such as sodium tripolyphosphate (STP), a hydrogel comprising fibrinogen may be cross-linkable in the presence of an enzyme such as thrombin, and a hydrogel comprising collagen, gelatin, agarose or chitosan may be cross-linkable in the presence of heat or a basic solution. In some embodiments hydrogel fibers may be generated through a precipitation reaction achieved via solvent extraction from the input material upon exposure to a cross-linker material that is miscible with the input material. Non-limiting examples of input materials that form fibers via a precipitation reaction include collagen and polylactic acid. Non-limiting examples of cross-linking materials that enable precipitation-mediated hydrogel fiber formation including polyethylene glycol (PEG) and alginate. Cross-linking of the hydrogel will increase the hardness of the hydrogel, in some embodiments allowing formation of a solidified hydrogel.

In some embodiments, a hydrogel comprises alginate. Alginate forms solidified colloidal gels (high water content gels, or hydrogels) when contacted with divalent cations. Any suitable divalent cation can be used to form a solidified hydrogel with an input material that comprises alginate. In the alginate ion affinity series $Cd^{2+}>Ba^{2+}>Cu^{2+}>Ca^{2+}>Ni^{2+}>Co^{2+}>Mn^{2+}$, $Ca^{2+}$ is the best characterized and most used to form alginate gels (Ouwerx, C. et al., Polymer Gels and Networks, 1998, 6(5):393-408). Studies indicate that Ca-alginate gels form via a cooperative binding of Ca' ions by poly G blocks on adjacent polymer chains, the so-called "egg-box" model (ISP Alginates, Section 3: Algin-Manufacture and Structure, in Alginates: Products for Scientific Water Control, 2000, International Specialty Products: San Diego, pp. 4-7). G-rich alginates tend to form thermally stable, strong yet brittle Ca-gels, while M-rich alginates tend to form less thermally stable, weaker but more elastic gels.

In some embodiments, a hydrogel comprises a depolymerized alginate as described in U.S. provisional patent application No. 62/437,601, the disclosure of which is incorporated by reference herein in its entirety.

In some embodiments, a hydrogel is cross-linkable using a free-radical polymerization reaction to generate covalent bonds between molecules. Free radicals can be generated by exposing a photoinitiator to light (often ultraviolet), or by exposing the hydrogel precursor to a chemical source of free radicals such as ammonium peroxodisulfate (APS) or potassium peroxodisulfate (KPS) in combination with N,N,N,N-Tetramethylethylenediamine (TEMED) as the initiator and catalyst respectively. Non-limiting examples of photo cross-linkable hydrogels include: methacrylated hydrogels, such as gelatin methacrylate (GEL-MA) or polyethylene (glycol) diacrylate-based (PEG-DA) hydrogels, which are used in cell biology due to their ability to crosslink in presence of free radicals after exposure to UV light and due to their inertness to cells. PEG-DA is commonly used as scaffold in tissue engineering, since polymerization occurs rapidly at room temperature and requires low energy input, has high water content, is elastic, and can be customized to include a variety of biological molecules.

Additional Components:

Input materials in accordance with embodiments of the invention can comprise any of a wide variety of natural or synthetic polymers that support the viability of living cells, including, e.g., laminin, fibrin, hyaluronic acid, poly(ethylene)glycol based gels, gelatin, chitosan, agarose, or combinations thereof. In particularly preferred embodiments, the subject bioink compositions are physiologically compatible, i.e., conducive to cell growth, differentiation and communication. In certain embodiments, an input material comprises one or more physiological matrix materials, or a combination thereof. By "physiological matrix material" is meant a biological material found in a native mammalian tissue. Non-limiting examples of such physiological matrix materials include: fibronectin, thrombospondin, glycosaminoglycans (GAG) (e.g., hyaluronic acid, chondroitin-6-sulfate, dermatan sulfate, chondroitin-4-sulfate, or keratin sulfate), deoxyribonucleic acid (DNA), adhesion glycoproteins, and collagen (e.g., collagen I, collagen II, collagen III, collagen IV, collagen V, collagen VI, or collagen XVIII).

Collagen gives most tissues tensile strength, and multiple collagen fibrils approximately 100 nm in diameter combine to generate strong coiled-coil fibers of approximately 10 μm in diameter. Biomechanical function of certain tissue constructs is conferred via collagen fiber alignment in an oriented manner. In some embodiments, an input material comprises collagen fibrils. An input material comprising collagen fibrils can be used to create a fiber structure that is formed into a tissue construct. By modulating the diameter of the fiber structure, the orientation of the collagen fibrils can be controlled to direct polymerization of the collagen fibrils in a desired manner.

For example, previous studies have shown that microfluidic channels of different diameters can direct the polymerization of collagen fibrils to form fibers that are oriented along the length of the channels, but only at channel diameters of 100 μm or less (Lee et al., 2006). Primary endothelial cells grown in these oriented matrices were shown to align in the direction of the collagen fibers. In another study, Martinez et al. demonstrate that 500 μm channels within a cellulose-bead scaffold can direct collagen and cell alignment (Martinez et al., 2012). In some embodiments, an input materials can be formed into a fiber structure that has a diameter that ranges from about 20 μm to about 500 μm, such as about 50 μm, about 75 μm, about 100 μm, about 125 μm, about 150 μm, about 175 μm, about 200 μm, about 225 μm, about 250 μm, about 275 μm, about 300 μm, about 325 μm, about 350 μm, about 375 μm, about 400 μm, about 425 μm, about 450 μm, or about 475 μm. By modulating the fiber diameter, the orientation of the collagen fibers within the fiber structure can be controlled. As such, the fiber structures, and the collagen fibers within them, can therefore be patterned to produce tissue constructs with a desired arrangement of collagen fibers, essential for conferring desired biomechanical properties on a 3D printed structure.

Mammalian Cell Types:

Input materials in accordance with embodiments of the invention can incorporate any mammalian cell type, including but not limited to stem cells (e.g., embryonic stem cells, adult stem cells, induced pluripotent stem cells), germ cells, endoderm cells (e.g., lung, liver, pancreas, gastrointestinal tract, or urogenital tract cells), mesoderm cells (e.g., kidney, bone, muscle, endothelial, or heart cells) and ectoderm cells (skin, nervous system, or eye cells), or any combination thereof.

In some embodiments, an input material can comprise: fibroblasts, chondrocytes, meniscus fibrochondrocytes, stem cells, bone marrow stromal (stem) cells, embryonic stem cells, mesenchymal stem cells, induced pluripotent stem cells, differentiated stem cells, tissue-derived cells, smooth muscle cells, skeletal muscle cells, cardiac muscle cells, epithelial cells, endothelial cells, myoblasts, chondroblasts, osteoblasts, osteoclasts, and any combinations thereof.

Cells can be obtained from donors (allogenic) or from recipients (autologous). Cells can also be from established cell culture lines, or can be cells that have undergone genetic engineering and/or manipulation to achieve a desired genotype or phenotype. In some embodiments, pieces of tissue can also be used, which may provide a number of different cell types within the same structure.

In some embodiments, cells can be obtained from a suitable donor, either human or animal, or from the subject into which the cells are to be implanted. Mammalian species include, but are not limited to, humans, monkeys, dogs, cows, horses, pigs, sheep, goats, cats, mice, rabbits, and rats. In one embodiment, the cells are human cells. In other embodiments, the cells can be derived from animals such as dogs, cats, horses, monkeys, or any other mammal.

Appropriate growth conditions for mammalian cells are well known in the art (Freshney, R. I. (2000) Culture of Animal Cells, a Manual of Basic Technique. Hoboken N.J., John Wiley & Sons; Lanza et al. Principles of Tissue Engineering, Academic Press; 2nd edition May 15, 2000; and Lanza & Atala, Methods of Tissue Engineering Academic Press; 1st edition October 2001). Cell culture media generally include essential nutrients and, optionally, additional elements such as growth factors, salts, minerals, vitamins, etc., that may be selected according to the cell type(s) being cultured. Particular ingredients may be selected to enhance cell growth, differentiation, secretion of specific proteins, etc. In general, standard growth media include Dulbecco's Modified Eagle Medium, low glucose (DMEM), with 110 mg/L pyruvate and glutamine, supplemented with 10-20% fetal bovine serum (FBS) or calf serum and 100 U/ml penicillin are appropriate as are various other standard media well known to those in the art. Growth conditions will vary depending on the type of mammalian cells in use and the tissue desired.

In some embodiments, cell-type specific reagents can be advantageously employed in the subject input materials for use with a corresponding cell type. For example, an extracellular matrix ("ECM") can be extracted directly from a tissue of interest and then solubilized and incorporated it into an input material to generate tissue-specific input materials for printed tissues. Such ECMs can be readily obtained from patient samples and/or are available commercially from suppliers such as zPredicta (rBone™, available at zpredicta.com/home/products).

Active Agents:

In some aspects, an input material in accordance with embodiments of the invention can comprise at least one active agent. Non-limiting examples of such active agents include TGF-β1, TGF-β2, TGF-β3, BMP-2, BMP-4, BMP-6, BMP-12, BMP-13, basic fibroblast growth factor, fibroblast growth factor-1, fibroblast growth factor-2, platelet-derived growth factor-AA, platelet-derived growth factor-BB, platelet rich plasma, IGF-I, IGF-II, GDF-5, GDF-6, GDF-8, GDF-10, vascular endothelial cell-derived growth factor, pleiotrophin, endothelin, nicotinamide, glucagon like peptide-I, glucagon like peptide-II, parathyroid hormone, tenascin-C, tropoelastin, thrombin-derived peptides, laminin, biological peptides containing cell-binding domains and biological peptides containing heparin-binding domains, therapeutic agents, and any combinations thereof.

The term "therapeutic agents" as used herein refers to any chemical moiety that is a biologically, physiologically, or pharmacologically active substance that acts locally or systemically in a subject. Non-limiting examples of therapeutic agents, also referred to as "drugs", are described in well-known literature references such as the Merck Index, the Physician's Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. In some embodiments, one or more therapeutic agents can be used, which are capable of being released from an input material described herein into adjacent tissues or fluids upon implantation to a subject. Examples of therapeutic agents include, but are not limited to, antibiotics, anesthetics, any therapeutic agents that promote regeneration or tissue healing, or that reduce pain, infection, or inflammation, or any combination thereof.

Additional active agents can include, but are not limited to, proteins, peptides, nucleic acid analogues, nucleotides, oligonucleotides, nucleic acids (DNA, RNA, siRNA), peptide nucleic acids, aptamers, antibodies or fragments or portions thereof, antigens or epitopes, hormones, hormone antagonists, growth factors or recombinant growth factors and fragments and variants thereof, cytokines, enzymes, antibiotics or antimicrobial compounds, anti-inflammation agent, antifungals, antivirals, toxins, prodrugs, small molecules, drugs (e.g., drugs, dyes, amino acids, vitamins, antioxidants) or any combination thereof.

Non-limiting examples of antibiotics that are suitable for inclusion in an input material include: aminoglycosides (e.g., neomycin), ansamycins, carbacephem, carbapenems, cephalosporins (e.g., cefazolin, cefaclor, cefditoren, cefditoren, ceftobiprole), glycopeptides (e.g., vancomycin), macrolides (e.g., erythromycin, azithromycin), monobactams, penicillins (e.g., amoxicillin, ampicillin, cloxacillin, dicloxacillin, flucloxacillin), polypeptides (e.g., bacitracin, polymyxin B), quinolones (e.g., ciprofloxacin, enoxacin, gatifloxacin, ofloxacin, etc.), sulfonamides (e.g., sulfasalazine, trimethoprim, trimethoprim-sulfamethoxazole (co-trimoxazole)), tetracyclines (e.g., doxycyline, minocycline, tetracycline, etc.), chloramphenicol, lincomycin, clindamycin, ethambutol, mupirocin, metronidazole, pyrazinamide, thiamphenicol, rifampicin, thiamphenicl, dapsone, clofazimine, quinupristin, metronidazole, linezolid, isoniazid, fosfomycin, fusidic acid, or any combination thereof.

Non-limiting examples of antibodies include: abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, zanolimumab, or any combination thereof.

Non-limiting examples of enzymes suitable for use in an input material as described herein include: peroxidase, lipase, amylose, organophosphate dehydrogenase, ligases, restriction endonucleases, ribonucleases, DNA polymerases, glucose oxidase, and laccase.

Additional non-limiting examples of active agents that are suitable for use with the subject input materials include: cell growth media, such as Dulbecco's Modified Eagle Medium, fetal bovine serum, non-essential amino acids and antibiotics; growth and morphogenic factors such as fibroblast growth factor, transforming growth factors, vascular endothelial growth factor, epidermal growth factor, platelet derived growth factor, insulin-like growth factors), bone morphogenetic growth factors, bone morphogenetic-like proteins, transforming growth factors, nerve growth factors, and related proteins (growth factors are known in the art, see, e.g., Rosen & Thies, CELLULAR & MOLECULAR BASIS BONE FORMATION & REPAIR (R. G. Landes Co., Austin, Tex., 1995); anti-angiogenic proteins such as endostatin, and other naturally derived or genetically engineered proteins; polysaccharides, glycoproteins, or lipoproteins; anti-infectives such as antibiotics and antiviral agents, chemotherapeutic agents (i.e., anticancer agents), anti-rejection agents, analgesics and analgesic combinations, anti-inflammatory agents, steroids, or any combination thereof.

Additional Fluids:

Aspects of the invention include one or more buffer solutions. Buffer solutions in accordance with embodiments of the invention are miscible with an input material (e.g., a hydrogel) and do not crosslink the input material. In some embodiments, a buffer solution comprises an aqueous solvent. Non-limiting examples of buffer solutions include polyvinyl alcohol, water, glycerol, propylene glycol, sucrose, gelatin, or any combination thereof.

Buffer solutions in accordance with embodiments of the invention can have a viscosity that ranges from about 1 mPa·s to about 5,000 mPa·s, such as about 10, 20, 30, 40, 50, 60, 70, 80, 90, 100, 200, 300, 400, 500, 600, 700, 800, 900, 1,000, 1,250, 1,500, 1,750, 2,000, 2,250, 2,500, 2,750, 3,000, 3,250, 3,500, 3,750, 4,000, 4,250, 4,500, or 4,750 mPa·s. In some embodiments, the viscosity of a buffer solution can be modulated so that it matches the viscosity of one or more input materials.

Aspects of the invention include one or more sheath fluids. Sheath fluids in accordance with embodiments of the invention are fluids that can be used, at least in part, to envelope or "sheath" an input material being dispensed from a dispensing channel. In some embodiments, a sheath fluid comprises an aqueous solvent. Non-limiting examples of sheath fluids include polyvinyl alcohol, water, glycerol, propylene glycol, sucrose, gelatin, or any combination thereof. Sheath fluids in accordance with embodiments of the invention can have a viscosity that ranges from about 1 mPa·s to about 5,000 mPa·s, such as about 10, 20, 30, 40, 50, 60, 70, 80, 90, 100, 200, 300, 400, 500, 600, 700, 800, 900, 1,000, 1,250, 1,500, 1,750, 2,000, 2,250, 2,500, 2,750, 3,000, 3,250, 3,500, 3,750, 4,000, 4,250, 4,500, or 4,750 mPa·s. In some embodiments, the viscosity of a sheath fluid can be modulated so that it matches the viscosity of one or more input materials.

In some embodiments, a sheath fluid comprises a chemical crosslinking agent. In some embodiments, a chemical crosslinking agent comprises a divalent cation. Non-limiting examples of divalent cations include $Cd^{2+}$, $Ba^{2+}$, $Cu^{2+}$, $Ca^{2+}$, $Ni^{2+}$, $Co^{2+}$, or $Mn^{2+}$. In a preferred embodiment, $Ca^{2+}$ is used as the divalent cation. In some embodiments, the concentration of a divalent cation in the sheath fluid ranges from about 80 mM to about 140 mM, such as about 90, 100, 110, 120 or 130 mM.

Methods of Use:

Aspects of the invention include methods of printing a linear fiber structure, a planar structure comprising one or more fiber structures, or a three-dimensional (3D) structure comprising two or more layers of planar structures. In some embodiments, a method first comprises providing a design for a planar or 3D structure to be printed. The design can be created using commercially available CAD software. In some embodiments, the design comprises information regarding specific materials (e.g., for heterogeneous structures comprising multiple materials) to be assigned to specific locations in the structure(s) to be printed.

In some embodiments, a method comprises the use of a 3D printer, the printer comprising: a print head, a receiving surface for receiving material dispensed by the print head; and a positioning unit operably coupled to the receiving surface, the positioning unit for positioning the print head at a location in three dimensional space above the receiving surface. For example, various embodiments of the printing system provided herein may be used in a method of printing a planar or 3D structure.

Aspects of the methods comprise providing one or more input materials to be dispensed by the print head. In some embodiments, one or more cell types are compatible with, and optionally dispensed within, an input material. In some embodiments, a sheath fluid serves as a lubricating agent for lubricating movement of an input material within the print head. In some embodiments, a sheath fluid comprises a cross-linking agent for solidifying at least a portion of the hydrogel before or while it is dispensed from the print head.

Aspects of the methods comprise communicating the design to the 3D printer. In some embodiments, communication can be achieved, for example, by a programmable control processor. In some embodiments, the methods comprise controlling relative positioning of the print head and the receiving surface in three dimensional space, and simultaneously dispensing from the print head the sheath fluid and an input material, alone or in combination. In some embodiments, the materials dispensed from the print ahead are dispensed coaxially, such that the sheath fluid envelopes the input material. Such coaxial arrangement allows a cross-linking agent in the sheath fluid to solidify the input material, thereby resulting in a solidified fiber structure, which is dispensed from the printer head.

In some embodiments, a method comprises depositing a first layer of the dispensed fiber structure on a receiving surface, the first layer comprising an arrangement of the fiber structure specified by the design, and iteratively repeating the depositing step, depositing subsequent fiber structures onto the first and subsequent layers, thereby depositing layer upon layer of dispensed fiber structures in a geometric arrangement specified by the design to produce a 3D structure.

In some embodiments, a plurality of input materials, for example multiple hydrogels, at least some of which comprise one or more cell types, are deposited in a controlled sequence, thereby allowing a controlled arrangement of input materials and cell types to be deposited in a geometric arrangement specified by the design.

In some embodiments, a method comprises removing excess fluid from the receiving surface and optionally from the surface of the dispensed fiber structure. For example, the step of removing the excess fluid can be done continuously throughout the printing process, thereby removing excess fluid that may otherwise interfere with layering the dispensed fiber structures in the geometric arrangement provided by the design. Alternatively, the step of removing excess fluid can be done intermittently throughout the printing process in sequence with or simultaneously with one or more depositing steps. In some embodiments, removal of excess fluid is achieved by drawing the fluid off of the receiving surface and optionally off of a surface of a dispensed fiber structure. In some embodiments, removal of excess fluid is achieved by drawing excess fluid through the receiving surface, the receiving surface comprising pores sized to allow passage of the fluid. In some embodiments, removal of excess fluid is achieved by providing a fluid that evaporates after being dispensed from the dispensing orifice.

Aspects of the invention include methods of making a 3D structure comprising one or more input materials. The 3D structures find use in repairing and/or replacing at least a portion of a damaged or diseased tissue in a subject.

As described above, any suitable divalent cation can be used in conjunction with the subject methods to solidify a chemically crosslinkable input material, including, but not limited to, $Cd^{2+}$, $Ba^{2+}$, $Cu^{2+}$, $Ca^{2+}$, $Ni^{2+}$, $Co^{2+}$, or $Mn^{2+}$. In a preferred embodiment, $Ca^{2+}$ is used as the divalent cation. In one preferred embodiment, a chemically crosslinkable input material is contacted with a solution comprising $Ca^{2+}$ to form a solidified fiber structure. In some embodiments, the concentration of $Ca^{2+}$ in the sheath solution ranges from about 80 mM to about 140 mM, such as about 90, 100, 110, 120 or 130 mM.

In certain embodiments, an input material is solidified in less than about 5 seconds, such as less than about 4 seconds, less than about 3 seconds, less than about 2 seconds, or less than about 1 second.

Aspects of the invention include methods of depositing one or more input materials in a patterned manner, using software tools, to form layers of solidified structures that are formed into a multi-layered 3D tissue structure. In some embodiments, a multi-layered 3D tissue structure comprises a plurality of mammalian cells. Advantageously, by modulating the components (e.g., the mammalian cell type, cell density, matrix components, active agents) of the subject input materials, a multi-layered 3D tissue structure can be created using the subject methods, wherein the multi-layered 3D tissue structure has a precisely controlled composition at any particular location in three dimensional space. As such, the subject methods facilitate production of complex three dimensional tissue structures.

In some embodiments, the methods comprise simultaneously dispensing buffer solution and/or sheath fluid through the core channel, one or more input materials through the one or more shell channels, and sheath fluid through the sheath flow channel so as to form a hollow core in the printed fiber.

In some embodiments, the non-cross-linkable materials in the core channel comprise a buffer solution and the sheath fluid in the sheath flow channel comprises a chemical cross-linking agent, and the contacting occurs at the sheath fluid intersection to solidify an exterior surface of the stream of cross-linkable materials in the dispensing channel.

In some embodiments, the non-cross-linkable materials in the core channel comprise a chemical cross-linking agent and the sheath fluid in the sheath flow channel comprises an aqueous solvent, and the contacting occurs at the first fluidic focusing intersection to solidify an interior surface of the stream of cross-linkable materials in the dispensing channel.

In some embodiments, the non-cross-linkable materials in the core channel comprise a chemical cross-linking agent, and the sheath fluid in the sheath flow channel comprises a chemical cross-linking agent, and the contacting occurs at the first fluidic focusing intersection to solidify an interior surface of the stream of cross-linkable materials and at the sheath fluid intersection to solidify an exterior surface of the stream of cross-linkable materials in the dispensing channel.

In alternative embodiments, solid core-shell fibers can be made using the same or different cross-linkable materials in the core and in the shell channels, respectively. In the former embodiment, the crosslinker may crosslink the core material by means of diffusion, such as alginate hydrogel being crosslinked by Ca2+ ions, or alternatively may be crosslinked in the presence of light. In the latter embodiment, the core channel comprises a cross-linkable material that may be solidified some time after being dispensed from the print head (e.g. collagen, laminin, fibrinogen, chitosan, elastin, Matrigel, methacrylated gelatin, PEG diacrylate, and the like), while the shell channel comprises a different cross-linkable material that is solidified upon printing (e.g. via chemical or light).

In an exemplary embodiment, different concentrations of the same cross-linkable material (e.g. alginate) can be employed with a higher concentration present in the shell channel and a lower concentration present in the core channel, and using the same crosslinker in the sheath flow channel (e.g., Ca2+) serving to crosslink both layers. In this embodiment, the Ca2+ ions will first diffuse through the crosslinkable shell material before crosslinking the cross-linkable core material.

In another exemplary embodiment, a chemically cross-linkable material (e.g. alginate) can be used in the shell channel and a different material that is crosslinked with heat (e.g. collagen) can be used in the core channel, and the chemical crosslinker in the sheath flow channel will allow printing of a solid fiber with a liquid core, which can then be transferred to an incubator or other heat source for subsequent crosslinking of the core material.

Utility:

In some embodiments, structures generated using the systems and methods provided herein can be useful in the field of drug discovery, where, for example, determining cellular responses to various chemical compounds and compositions are of interest. Use of planar and 3D cell cultures fabricated using embodiments of the systems and methods provided herein can provide experimental conditions that more closely resemble in vivo cellular and tissue conditions relative to traditional 2D cell cultures. 3D arrangement of the cells can more closely mimic in vivo cell-cell interactions and responses to external stimuli, and the heterogeneous nature of the 3D structures that can be generated using the systems and methods provided herein permit study of tissues and potentially organs. It is contemplated that 3D cell-laden structures fabricated using embodiments of the systems and methods provided herein can provide a similar benefit to the cosmetics industry by offering an alternative means to testing cosmetic products.

In some embodiments, various aspects of the systems and methods provided herein are compatible with standard well-plate technology. Well-plates or well-plate inserts may be used with or as part of the print bed in the methods and systems provided herein. Various embodiments of the systems and methods provided herein are thus compatible with instruments and practices that utilize well-plates, allowing them to be readily integrated into existing process streams.

In some embodiments, one or more fluid channels within a subject print head are compatible with other microfluidic modules. For example, known microfluidic modules can be included in the print head of the systems provided herein, upstream of the dispensing orifice. Such modules may include, for example, cell counting, cell sorting, cell analyzing, and/or concentration gradient generating modules.

In some embodiments, throughput of 3D printing can be increased by adding to the systems additional print heads in parallel. Each print head comprising all of the elements required to print a multi-material structure, thus allowing several 3D structures to be printed simultaneously by including additional print heads in the system.

All patents and patent publications referred to herein are hereby incorporated by reference in their entirety.

Although the foregoing invention has been described in detail by way of illustration and example for purposes of clarity of understanding, it is readily apparent to those of ordinary skill in the art in light of the teachings of this invention that certain changes and modifications can be made thereto without departing from the spirit or scope of the appended claims.

The LOP™ enables multi-material switching, thus the composition of the vessel wall (cell type and biomaterial composition) can be modified along the length of the channel while continuously printing. An example of this is to reproduce the biological structure and function of a kidney tubule, the wall composition at the proximal end will be different to that at the distal end. Or in a perfusable printed 3D liver tissue where the vessel wall may be lined with portal arteriole endothelial cells of low permeability at the larger opening end of the vessel, and with more permeable sinusoidal endothelial cells further into the vessel where the channel is narrower to model the sinusoid. Similar to the liver tissue, it is desirable to investigate the interaction of the contents of the perfused channel with different stromal cell types outside the channel in one or more of the outer shells. This could be applied to generate a multi-tissue model of toxicity combined with the effects of shear flow. A single tissue could be printed with the cellular contents of the shell of the fiber being switched along its length to generate a coded hollow fiber with different regions that correspond to different organ types. This switching of shell contents is not possible with a non-microfluidic syringe-based system.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

The invention claimed is:

1. A print head for producing a fiber structure, the print head comprising:
    a dispensing channel comprising a proximal end having a first diameter and a distal end having a second diameter;
    a dispensing orifice located at the distal end of the dispensing channel;
    a core channel having a third diameter converging with the dispensing channel at the proximal end of the dispensing channel, wherein the third diameter of the core channel is less than the first and second diameters of the dispensing channel;
    a first shell channel converging with the core channel and the dispensing channel at a first fluidic focusing intersection at the proximal end of the dispensing channel, wherein the first shell channel comprises a plurality of sub-channels that converge toward the dispensing channel via a first fluidic focusing chamber disposed within the print head, and wherein the first fluidic focusing chamber comprises a conical frustum shape configured to focus fluid toward the dispensing channel;
    a sheath flow channel converging with the dispensing channel at a sheath fluid intersection located between the first fluidic focusing intersection and the distal end of the dispensing channel, wherein the sheath flow channel comprises a plurality of sheath flow sub-channels that converge toward the dispensing channel via a sheath fluid chamber, wherein the sheath fluid chamber comprises a conical frustum shape configured to focus fluid toward the dispensing channel, wherein the second diameter is equal to the smallest diameter of the conical frustum shape at the outlet of the sheath fluid chamber where the diameter of the dispensing channel increases from said first diameter to said second diameter;
    wherein the core channel, the first shell channel and the sheath flow channel are in fluid communication with the dispensing channel.

2. The print head according to claim 1, wherein the print head is configured to dispense non-cross-linkable materials through the core channel.

3. The print head according to claim 1, wherein the first diameter is substantially identical to the smallest diameter of the conical frustum shape at the outlet of the first fluidic focusing chamber.

4. The print head according to claim 1, further comprising a second shell channel converging with the dispensing channel at a second fluidic focusing intersection located between the first fluidic focusing intersection and the sheath fluid intersection.

5. The print head according to claim 1, wherein the sheath flow channel comprises a sheath fluid input orifice and a control valve.

6. The print head according to claim 5, wherein the print head is configured to dispense a sheath fluid comprising a chemical cross-linking agent through the sheath flow channel.

7. The print head according claim 1, wherein the print head comprises at least two core sub-channels, which converge to form a first fluid focusing inlet having the third diameter.

8. The print head according to claim 7, wherein a first core sub-channel comprises a sheath fluid input orifice and a first control valve, and a second core sub-channel comprises a buffer solution input orifice and a second control valve.

9. The print head according to claim 1, wherein the first shell channel is concentrically disposed around a distal end of the core channel.

10. The print head according to claim 9, wherein the distal end of the core channel comprises a tube disposed within the first shell channel in the print head.

* * * * *